US010975163B2

(12) United States Patent
Madiyalakan et al.

(10) Patent No.: US 10,975,163 B2
(45) Date of Patent: Apr. 13, 2021

(54) METHODS OF INCREASING DELIVERY OF ANTI-CANCER AGENTS TO TARGETS

(71) Applicant: Oncoquest, Inc., Edmonton (CA)

(72) Inventors: Ragupathy Madiyalakan, Edmonton (CA); Christopher F. Nicodemus, Charlestown, MA (US); Michael A Hollingsworth, Omaha, NE (US)

(73) Assignee: ONCOQUEST PHARMACEUTICALS INC.

( * ) Notice: Subject to any disclaimer, the term of this patent is extended or adjusted under 35 U.S.C. 154(b) by 115 days.

(21) Appl. No.: 15/541,451

(22) PCT Filed: Jan. 15, 2016

(86) PCT No.: PCT/CA2016/050035
§ 371 (c)(1),
(2) Date: Jul. 3, 2017

(87) PCT Pub. No.: WO2016/112466
PCT Pub. Date: Jul. 21, 2016

(65) Prior Publication Data
US 2018/0002441 A1  Jan. 4, 2018

Related U.S. Application Data

(60) Provisional application No. 62/103,758, filed on Jan. 15, 2015.

(51) Int. Cl.
*A61K 39/395* (2006.01)
*C07K 16/30* (2006.01)
*A61K 31/7068* (2006.01)
*C07K 16/28* (2006.01)
*A61K 39/00* (2006.01)

(52) U.S. Cl.
CPC ...... *C07K 16/3092* (2013.01); *A61K 31/7068* (2013.01); *A61K 39/39558* (2013.01); *C07K 16/2827* (2013.01); *A61K 2039/507* (2013.01); *C07K 2317/52* (2013.01)

(58) Field of Classification Search
None
See application file for complete search history.

(56) References Cited

U.S. PATENT DOCUMENTS

| | | | | |
|---|---|---|---|---|
| 6,716,966 B1 * | 4/2004 | Madiyalakan | ...... | A61K 41/0057 530/387.1 |
| 7,147,850 B2 * | 12/2006 | Madiyalakan | ...... | A61K 41/0057 424/131.1 |
| 9,587,032 B2 * | 3/2017 | Mollick | ............ | C07K 16/2887 |
| 2012/0058126 A1 * | 3/2012 | Pytowski | ........... | A61K 39/3955 424/172.1 |
| 2012/0171203 A1 * | 7/2012 | Yan | ................. | A61K 39/39558 424/134.1 |
| 2013/0150385 A1 * | 6/2013 | Blackman | ............. | A61K 45/06 514/266.4 |
| 2014/0370001 A1 | 12/2014 | Mollick et al. | | |

FOREIGN PATENT DOCUMENTS

WO   WO 2014/201212 A1   12/2014

OTHER PUBLICATIONS

Singer and Jarolim. IgE-based Immunotherapy of Cancer—A Comparative Oncology Approach. J Carcinog Mutagen. May 31, 2014;5(3):1000176. (Year: 2014).*
Singer and Jarolim. IgE-based immunotherapy of cancer: challenges and chances. Allergy. Feb. 2014;69(2):137-49 (Year: 2014).*
Daniels et al. Targeting HER2/neu with a fully human IgE to harness the allergic reaction against cancer cells. Cancer Immunol Immunother. Jul. 2012 ; 61(7): 991-1003. (Year: 2012).*
Teo, Zhao Ying Pearline. Using the allergic immune system to target cancer: Tumor specific IgE antibodies as cancer therapeutics. Dissertation Abstract. Dissertation Abstracts International, (2008) vol. 70, No. 1 B. pp. 1-2 (Year: 2008).*
Fu et al., Immunoglobulin E antibodies from pancreatic cancer patients mediate antibody-dependent cell-mediated cytotoxicity against pancreatic cancer cells. Clin Exp Immunol. Sep. 2008;153(3):401-9. (Year: 2008).*
Jensen-Jarolim et al. AllergoOncology: the role of IgE-mediated allergy in cancer. Allergy. Oct. 2008 ; 63(10): 1255-1266. (Year: 2008).*
Josephs et al. IgE immunotherapy: a novel concept with promise for the treatment of cancer. MAbs. Jan.-Feb. 2014;6(1):54-72. (Year: 2014).*
Karagiannis et al., Characterisation of an engineered trastuzumab IgE antibody and effector cell mechanisms targeting HER2/neu-positive tumour cells. Cancer Immunol Immunother. Jun. 2009 ; 58(6): 915-930. (Year: 2009).*
Karagiannis et al., Recombinant IgE antibodies for passive immunotherapy of solid tumours: from concept towards clinical application. Cancer Immunol Immunother (2012) 61:1547-1564. (Year: 2012).*
Koers, Alexander Magnus Maria. Radiolabelling and biodistribution of IgE antibodies. Ph.D dissertation, King's College, London, Sep. 2014, pp. 1-206. (Year: 2014).*
Nigro et al., Role and Redirection of IgE against Cancer. Antibodies 2013, 2, 371-391. (Year: 2013).*

(Continued)

*Primary Examiner* — Maher M Haddad
(74) *Attorney, Agent, or Firm* — McDonnell Boehnen Hulbert & Berghoff LLP

(57) ABSTRACT

The present invention provides compositions and methods for increasing the permeability of a stroma around a neoplasm, and particularly to cancer cells associated with solid tumors. In one embodiment, combining a therapeutic IgE antibody with an anti-cancer agent in accordance with the invention increases the delivery of the anticancer agent to the site of, for example, a solid tumor in a subject. In one embodiment, combining a therapeutic IgE antibody with an anti-cancer agent in accordance with the invention potentiates a tumor's responsiveness and sensitivity to the anti-cancer agent.

8 Claims, 8 Drawing Sheets
Specification includes a Sequence Listing.

(56) References Cited

OTHER PUBLICATIONS

Teo et al. Using the allergic immune system to target cancer: activity of IgE antibodies specific for human CD20 and MUC1. Cancer Immunol Immunother. Dec. 2012;61(12):2295-309 (Year: 2012).*
Uchida et al. Inhibition of the MUC1-C oncoprotein is synergistic with cytotoxic agents in the treatment of breast cancer cells. Cancer Biology & Therapy 14:2, 127-134; Feb. 2013 (Year: 2013).*
Chauhan et al. Combined Staining of TAG-72, MUC1, and CA125 Improves Labeling Sensitivity in Ovarian Cancer: Antigens for Multi-targeted Antibody-guided Therapy. Journal of Histochemistry & Cytochemistry. vol. 55(8): 867-875, 2007. (Year: 2007).*
Roy et al. MUC1 enhances invasiveness of pancreatic cancer cells by inducing epithelial to mesenchymal transition. Oncogene. Mar. 24, 2011; 30(12): 1449-1459. (Year: 2011).*
Nagato et al. Combinatorial Immunotherapy of Polyinosinic-Polycytidylic Acid and Blockade of Programmed Death-Ligand 1 Induce Effective CD8 T-cell Responses against Established Tumors. Clin Cancer Res. Mar. 1, 2014; 20(5): 1223-1234, published on line Jan. 3, 2014). (Year: 2014).*
Singer J, Jarolim EJ (2014) IgE-based Immunotherapy of Cancer—A Comparative Oncology Approach. J Carcinog & Mutagen 5: 176. (Year: 2014).*
Karagiannis et al.IgE-Antibody-Dependent Immunotherapy of Solid Tumors: Cytotoxic and Phagocytic Mechanisms of Eradication of Ovarian Cancer Cells. J Immunol 2007; 179:2832-2843. (Year: 2007).*
Daniels-Wells, et al., "A Novel IgE Antibody Targeting Prostate-Specific Antigen as a Potential Prostate Cancer Therapy," BMC Cancer, Apr. 2013, vol. 13, 195-207.
Neese et al., "Stromal Biology and Therapy in Pancreatic Cancer," Gut, Jun. 2011, vol. 60, 861-868.
Nicodemus et al., "Antibody-Based Immunotherapy of Solid Cancers: Progress and Possibilities," Immunotherapy, Aug. 2015, vol. 7, 923-939.
Provenzano, et al., "Enzymatic Targeting of the Stroma Ablates Barriers to treatment of Pancreatic Ductal Adenocarcinoma," Cancer Cell, Mar. 2012, vol. 21, 418-429.
Sertl, et al., "Passive Sensitization and Antigen Challenge Increase Vascular Permeability in Rat Airways," Am. Rev. Respir. Dis., Nov. 1988, vol. 138, 1295-1299.
Stromnes et al., "Stromal Reengineering to Treat Pancreas Cancer," Carcinogenisis, Jul. 2014, vol. 35, 1451-1460.
International Search Report in PCT/CA2016/050035, dated Mar. 22, 2016.
A. Wang-Gillam, "Targeting Stroma: A Tale of Caution", Journal of Clinical Oncology, 37:1041-1044 (2019).
Ackerman, et al., "Outcomes of Patients with Metastatic Melanoma Treated with Immunotherapy Prior to or After BRAF Inhibitors," Cancer, 120:1695-1701 (2014).
Ascierto, et al., "Sequential Treatment with Ipilimumab and BRAF Inhibitors in Patients with Metastatic Melanoma: Data from the Italian Cohort of the Ipilmumab Expanded Access Program," Cancer Investigation, 32:144-149 (2014).
Mehla, et al., "Combination of mAb-AR20.5, anti-PD-L1 and PolyICLC inhibits tumor progression and prolongs survival of MUC1.Tg mice challenged with pancreatic tumors", Cancer Immunology, Immunotherapy, 1-13 (2017).
Lynch, et al., "Ipilimumab in Combination with Paclitaxel and Carboplatin as First-Line Treatment in Stave IIB/IV non-Small-Cell Lung Cancer: Results from a Randomized, Double-Blind, Multicenter Phase II Study," Journal of Clinical Oncology, vol. 30:2046-2054 (2012).
Lynch, et al., "Passive Local Anaphylaxis: Demonstration of Antitumor Activity and Complementation of Intratumor BCG," J. Natl. Cancer Institute, 58:1093-1098 (1977).
Reck, et al., "Ipilimumab in combination with paclitaxel and carboplatin as first-line therapy in extensive-disease-small-lung cancer: results from a randomized, double-blind, multicenter phase 2 trial," Annals of Oncology, 24:76-83 (2013).

* cited by examiner

METHODS OF INCREASING DELIVERY OF ANTI-CANCER AGENTS TO TARGETS

CROSS-REFERENCE TO RELATED APPLICATIONS

This application is a U.S. National Phase of PCT/CA2016/050035, international filing date Jan. 15, 2016, which claims priority under 35 USC § 119(e) of U.S. provisional patent application 62/103,758, filed on Jan. 15, 2015, the specification each of which is are hereby incorporated by reference.

BACKGROUND OF THE INVENTION

Conventional cancer diagnosis and therapies to date have attempted to selectively detect and eradicate neoplastic cells that are largely fast-growing (i.e., cells that form the tumor bulk). Despite the availability of a large variety of antineoplastic agents, these therapies have many drawbacks. Solid malignancies have supportive connective tissue components derived from non-malignant precursors that protect and nourish growing malignant cells. These stromal tissues prevent antineoplastic agents (e.g. chemotherapeutics) agents from effectively reaching malignant cells, and force doses of antineoplastic treatments to be pushed to upper limits of tolerability. For example, chemotherapeutic agents are notoriously toxic due to non-specific side effects including bone marrow depression, immunosuppression, and gastrointestinal distress, etc. Therefore, compositions and methods that increase the effectiveness of an anti-cancer treatment regimen are still needed.

SUMMARY OF THE INVENTION

According to an embodiment, there is provided a method for increasing the permeability of a stroma around a neoplasm in a subject comprising administering to the subject, an effective amount of at least one IgE antibody specific for a cancer antigen, an antigen present in or around the stroma of a neoplasm, or a combination thereof.

According to another embodiment, there is provided a method of increasing the delivery of an anti-cancer agent to a neoplasm comprising the step of co-administering to a subject, an effective amount of at least one IgE antibody specific for a cancer antigen, an antigen present in or around a stroma of a tumor, or a combination thereof and at least one anti-cancer agent.

According to another embodiment, there is provided a method of treating cancer comprising the step of co-administering to a subject, an effective amount of at least one IgE antibody specific for a cancer antigen, an antigen present in or around a stroma of a tumor, or a combination thereof and at least one anti-cancer agent.

According to another embodiment, there is provided a method of inhibiting the growth of a tumor comprising the step of contacting the tumor with an effective amount of at least one IgE antibody specific for a cancer antigen, an antigen present in or around a stroma of a tumor, or a combination thereof and at least one anti-cancer agent.

According to another embodiment, there is provided a method of increasing the delivery of an anti-cancer agent to a tumor in a subject comprising the step of co-administering to the subject, an effective amount of at least one IgE antibody specific for a cancer antigen, an antigen present in or around a stroma of a tumor, or a combination thereof and at least one anti-cancer agent.

According to another embodiment, there is provided a method for modulating a stroma around a solid tumor comprising the step of contacting the tumor with an effective amount of at least one IgE antibody specific for a cancer antigen, an antigen present in or around the stroma of a tumor, or a combination thereof.

According to another embodiment, there is provided a method of potentiating a tumor's susceptibility to an anti-cancer agent in a subject comprising the steps of administering to a subject, an effective amount of at least one IgE antibody specific for a cancer antigen, an antigen present in or around a stroma of a tumor, or a combination thereof in combination with the anti-cancer agent.

The IgE antibody may be specific to a cancer antigen or an antigen associated with a neoplasm's microenvironment.

The method may further comprise administering an anti-cancer agent to the subject.

The anti-cancer agent may be selected from: anti-neoplastic agents, immunotherapeutic agents, radiation, photosensitizers, gene therapeutic agents and combinations thereof.

The IgE antibody and the anti-cancer agent may be administered simultaneously or sequentially.

The IgE antibody may be administered simultaneously and in the same composition as the anti-cancer agent wherein the anti-cancer agent may be selected from antineoplastic agents, immunotherapeutic agents, photosensitizers, or gene therapeutic agents.

The IgE antibody may be conjugated to the anti-cancer agent.

The IgE antibody and the anti-cancer agent may be administered sequentially.

The IgE antibody and the anti-cancer agent may be administered sequentially, wherein the therapeutic IgE antibody may be administered at least about 1 minute to about 2 weeks prior to, or after, administration of the anti-cancer agent.

The neoplasm may be a solid tumor.

The neoplasm may be a solid tumor, wherein the anti-cancer agent may be an anti-neoplastic agent, and wherein increased delivery of the anti-neoplastic agent to the tumor may be measured by an increase in the uptake of polydextrans of different size in the tumor or tumor stroma.

The neoplasm may be a solid tumor, wherein the anti-cancer agent may be an immunotherapeutic agent, and wherein increased permeability may be measured by an increase in the presence of infiltrating lymphocytes in the tumor or a tumor stroma.

The neoplasm may be a solid tumor, wherein the anti-cancer agent may be radiation, and wherein increased permeability may be measured by a decrease in the size of the tumor as measured by imaging studies.

The neoplasm may be a solid tumor, wherein the anti-cancer agent may be a gene therapeutic agent, and wherein increased delivery of the gene therapeutic agent to the tumor may be measured by an increase in an immune response in the microenvironment of the tumor.

The IgE antibody may be an antibody specific to MUC1.

The antibody specific to MUC1 may bind an epitope of MUC1 selected from SEQ ID NO: 5.

The heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

The heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

The antibody specific to MUC1 may be mAb 3C6.hIgE, mAb 4H5.hIgE or a combination thereof.

The neoplasm may be pancreatic cancer, gastric cancer, colorectal cancer, ovarian cancer, breast cancer or lung cancer.

The neoplasm may be in vivo or in vitro.

The increase in the permeability around the stroma results in a) an increase in the therapeutic index of the anti-cancer agent; b) amelioration of at least one adverse effect of the anticancer agent; c) reduction in the amount of anti-cancer agent used in treatment; d) increase in the permeability of tumor stroma; and e) depletion of the tumor stroma.

The anti-cancer agent may be contacted with the tumor after the IgE antibody may be contacted with the tumor.

The anti-cancer agent may be contacted with the tumor before the IgE antibody may be contacted with the tumor.

The anticancer agent may be administered to the subject simultaneously with the IgE antibody.

The IgE antibody may be specific for an antigen associated with a tumor stroma.

According to another embodiment, there is provided a use of an effective amount of at least one IgE antibody specific for a cancer antigen, an antigen present in or around a stroma of a tumor, or a combination thereof to increase the permeability of the stroma around a solid tumor in a subject in need thereof.

According to another embodiment, there is provided a use of an effective amount of at least one IgE antibody specific for a cancer antigen, an antigen present in or around a stroma of a tumor, or a combination thereof and at least one anti-cancer agent to increase the delivery of the anti-cancer agent to a neoplasm in a subject in need thereof.

According to another embodiment, there is provided a use of an effective amount of at least one IgE antibody specific for a cancer antigen, an antigen present in or around a stroma of a tumor, or a combination thereof, and at least one anti-cancer agent for treatment of cancer in a subject in need thereof.

According to another embodiment, there is provided a use of an effective amount of at least one IgE antibody and specific for a cancer antigen, an antigen present in or around a stroma of a tumor, or a combination thereof, and at least one anti-cancer agent to inhibit the growth of a tumor in a subject in need thereof.

According to another embodiment, there is provided a use of an effective amount of at least one IgE antibody specific for a cancer antigen, an antigen present in or around a stroma of a tumor, or a combination thereof and at least one anti-cancer agent to increase the delivery of an anti-cancer agent to a tumor in a subject in need thereof.

According to another embodiment, there is provided a use of an effective amount of at least one IgE antibody specific for a cancer antigen, an antigen present in or around a stroma of a tumor, or a combination thereof to modulate the stroma around a solid tumor in a subject in need thereof.

According to another embodiment, there is provided a use of an effective amount of at least one IgE antibody specific for a cancer antigen, an antigen present in or around a stroma of a tumor, or a combination thereof in combination with the anti-cancer agent to potentiate a tumor's susceptibility to an anti-cancer agent in a subject in need thereof.

The IgE antibody may be specific to a cancer antigen or an antigen associated with a neoplasm's microenvironment.

The use may further comprise the use of an anticancer agent.

The anti-cancer agent may be selected from: anti-neoplastic agents, immunotherapeutic agents, radiation, photo-sensitizers, gene therapeutic agents and combinations thereof.

The IgE antibody and the anti-cancer agent may be for administration simultaneously or sequentially.

The IgE antibody may be for administration simultaneously and in the same composition as the anti-cancer agent wherein the anti-cancer agent may be selected from anti-neoplastic agents, immunotherapeutic agents, photosensitizers, or gene therapeutic agents.

The IgE antibody may be conjugated to the anti-cancer agent.

The IgE antibody and the anti-cancer agent may be for administration sequentially.

The IgE antibody and the anti-cancer agent may be for administration sequentially, wherein the therapeutic IgE antibody may be for administration at least about 1 minute to about 2 weeks prior to, or after, administration of the anti-cancer agent.

The neoplasm may be a solid tumor.

The neoplasm may be a solid tumor, wherein the anti-cancer agent may be an anti-neoplastic agent, and wherein an increase in permeability may be determined by an increase in the uptake of polydextrans of different size in the tumor or tumor stroma.

The neoplasm may be a solid tumor, wherein the anti-cancer agent may be an immunotherapeutic agent, and wherein an increase in permeability may be determined by an increase in the presence of infiltrating lymphocytes in the tumor or tumor stroma.

The neoplasm may be a solid tumor, wherein the anti-cancer agent may be radiation, and wherein an increase in permeability may be determined by a decrease in the size of the tumor as measured by imaging studies.

The neoplasm may be a solid tumor, wherein the anti-cancer agent may be a gene therapeutic agent, and wherein an increase in permeability may be determined by an increase in an immune response in the microenvironment of the tumor.

The IgE antibody may be an antibody specific to MUC1.

The antibody specific to MUC1 may bind an epitope of MUC1 selected from SEQ ID NO: 5.

The heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

The heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

The antibody specific to MUC1 may be mAb 3C6.hIgE, mAb 4H5.hIgE or a combination thereof.

The neoplasm may be pancreatic cancer, gastric cancer, colorectal cancer, ovarian cancer, breast cancer or lung cancer.

The tumor may be in vivo or in vitro.

The increase in permeability around the stroma may result in a) an increase in the therapeutic index of the anti-cancer agent; b) amelioration of at least one adverse effect of the anticancer agent; c) reduction in the amount of anti-cancer agent for use in treatment; d) increase in the permeability of tumor stroma; and e) depletion of the tumor stroma.

The anticancer agent may be for use after the IgE antibody.

The anti-cancer agent may be for use before the IgE antibody.

The anti-cancer agent may be for use simultaneously with the IgE antibody.

The IgE antibody may be specific for an antigen associated with a tumor stroma.

According to another embodiment, there is provided a composition for use in increasing the permeability of a stroma around a neoplasm in a subject in need thereof, the composition comprising an effective amount of at least one IgE antibody specific for a cancer antigen, an antigen present in or around the stroma of a tumor, or a combination thereof, and pharmaceutically acceptable excipients.

According to another embodiment, there is provided a composition for use in increasing the delivery of the anti-cancer agent to a neoplasm in a subject in need thereof, the composition comprising an effective amount of at least one IgE antibody specific for a cancer antigen, an antigen present in or around a stroma of a tumor, or a combination thereof and at least one anti-cancer agent.

According to another embodiment, there is provided a composition for use in treatment of cancer in a subject in need thereof, the composition comprising an effective amount of at least one IgE antibody specific for a cancer antigen, an antigen present in or around a stroma of a tumor, or a combination thereof, and at least one anti-cancer agent.

According to another embodiment, there is provided a composition for use in inhibiting the growth of a tumor in a subject in need thereof, the composition comprising an effective amount of at least one IgE antibody and specific for a cancer antigen, an antigen present in or around a stroma of a tumor, or a combination thereof, and at least one anti-cancer agent.

According to another embodiment, there is provided a composition for use in increasing the delivery of an anti-cancer agent to a tumor in a subject in need thereof, the composition comprising an effective amount of at least one IgE antibody specific for a cancer antigen, an antigen present in or around a stroma of a tumor, or a combination thereof and at least one anti-cancer agent.

According to another embodiment, there is provided a composition for use in modulating a stroma around a solid tumor in a subject in need thereof, the composition comprising an effective amount of at least one IgE antibody specific for a cancer antigen, an antigen present in or around the stroma of a tumor, or a combination thereof.

According to another embodiment, there is provided a composition for use in potentiating a tumor's susceptibility to an anti-cancer agent in a subject in need thereof, the composition comprising an effective amount of at least one IgE antibody specific for a cancer antigen, an antigen present in or around a stroma of a tumor, or a combination thereof in combination with the anti-cancer agent.

The IgE antibody may be specific to a cancer antigen or an antigen associated with a neoplasm's microenvironment.

The neoplasm may be a solid tumor.

The composition may further comprise an anticancer agent.

The anti-cancer agent may be selected from: anti-neoplastic agents, immunotherapeutic agents, radiation, photosensitizers, gene therapeutic agents and combinations thereof.

The IgE antibody and the anti-cancer agent may be for administration simultaneously.

The IgE antibody may be conjugated to the anti-cancer agent.

The neoplasm may be a solid tumor, wherein the anti-cancer agent may be an anti-neoplastic agent, and wherein an increase in permeability may be determined by an increase in the uptake of polydextrans of different size in the tumor or tumor stroma.

The neoplasm may be a solid tumor, wherein the anti-cancer agent may be an immunotherapeutic agent, and wherein an increase in permeability may be determined by an increase in the presence of infiltrating lymphocytes in the tumor or tumor stroma.

The neoplasm may be a solid tumor, wherein the anti-cancer agent may be radiation, and wherein an increase in permeability may be determined by a decrease in the size of the tumor as measured by imaging studies.

The neoplasm may be a solid tumor, wherein the anti-cancer agent may be a gene therapeutic agent, and wherein an increase in permeability is determined by an increase in an immune response in the microenvironment of the tumor.

The IgE antibody may be an antibody specific to MUC1.

The antibody specific to MUC1 may bind an epitope of MUC1 selected from SEQ ID NO: 5.

The heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

The heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

The antibody specific to MUC1 may be mAb 3C6.hIgE, mAb 4H5.hIgE or a combination thereof.

The neoplasm may be pancreatic cancer, gastric cancer, colorectal cancer, ovarian cancer, breast cancer or lung cancer.

The neoplasm may be in vivo or in vitro.

The increase in permeability around said stroma may result in a) an increase in the therapeutic index of the anti-cancer agent; b) amelioration of at least one adverse effect of the anticancer agent; c) reduction in the amount of anti-cancer agent for use in treatment; d) increase in the permeability of tumor stroma; and e) depletion of the tumor stroma.

The anticancer agent may be for use after the IgE antibody.

The anti-cancer agent may be for use before the IgE antibody.

The anticancer agent may be for use simultaneously with the IgE antibody.

The IgE antibody may be specific for an antigen associated with a tumor stroma.

According to another embodiment, there is provided a kit for use in increasing the permeability of a stroma around a neoplasm in a subject in need thereof, the kit comprising an effective amount of at least one IgE antibody specific for a cancer antigen, an antigen present in or around a stroma of a tumor, or a combination thereof; and instructions on how to use the kit.

According to another embodiment, there is provided a kit for use in increasing the delivery of the anti-cancer agent to a neoplasm in a subject in need thereof, the kit comprising a therapeutically effective amount of at least one therapeutic IgE antibody specific for a cancer antigen, an antigen present in or around a stroma of a tumor, or a combination thereof; at least one anti-cancer agent; and instructions on how to use the kit.

According to another embodiment, there is provided a kit for use in treatment of cancer in a subject in need thereof, the kit comprising an effective amount of at least one IgE antibody specific for a cancer antigen, an antigen present in or around a stroma of a tumor, or a combination thereof; at least one anti-cancer agent; and instructions on how to use the kit.

According to another embodiment, there is provided a kit for use in inhibiting cancer tumor growth in a patient in need thereof, the kit comprising an effective amount of at least one therapeutic IgE antibody specific for a cancer antigen, an antigen present in or around a stroma of a tumor, or a combination thereof; at least one anti-cancer agent; and instructions on how to use the kit.

According to another embodiment, there is provided a kit for use in increasing the delivery of an anti-cancer agent to a tumor in a subject in need thereof, the kit comprising an effective amount of at least one IgE antibody specific for a cancer antigen, an antigen present in or around a stroma of a tumor, or a combination thereof; at least one anti-cancer agent; and instructions on how to use the kit.

According to another embodiment, there is provided a kit for use in increasing the delivery of an anti-cancer agent to a tumor in a subject in need thereof, the kit comprising an effective amount of at least one IgE antibody specific for a cancer antigen, an antigen present in or around a stroma of a tumor, or a combination thereof; at least one anti-cancer agent; and instructions on how to use the kit.

According to another embodiment, there is provided a kit for use in modulating a stroma around a solid tumor in a subject in need thereof, the kit comprising an effective amount of at least one IgE antibody specific for a cancer antigen, an antigen present in or around a stroma of a tumor, or a combination thereof; at least one anti-cancer agent; and instructions on how to use the kit.

According to another embodiment, there is provided a kit for use in potentiating a tumor's susceptibility to an anti-cancer agent in a subject in need thereof, the kit comprising an effective amount of at least one IgE antibody specific for a cancer antigen, an antigen present in or around a stroma of a tumor, or a combination thereof; at least one anti-cancer agent; and instructions on how to use the kit.

The IgE antibody may be specific to a cancer antigen or an antigen associated with a neoplasm's microenvironment.

The kit may further comprise an anticancer agent.

The anti-cancer agent may be selected from: anti-neoplastic agents, immunotherapeutic agents, radiation, photosensitizers, gene therapeutic agents and combinations thereof.

The IgE antibody and the anti-cancer agent may be for administration simultaneously.

The neoplasm may be a solid tumor.

The IgE antibody may be conjugated to the anti-cancer agent.

The neoplasm may be a solid tumor, wherein the anti-cancer agent may be an anti-neoplastic agent, and wherein an increase in permeability may be determined by an increase in the uptake of polydextrans of different size in the tumor or tumor stroma.

The neoplasm may be a solid tumor, wherein the anti-cancer agent may be an immunotherapeutic agent, and wherein an increase in permeability is determined by an increase in the presence of infiltrating lymphocytes in the tumor or tumor stroma.

The neoplasm may be a solid tumor, wherein the anti-cancer agent may be radiation, and wherein an increase permeability may be determined by a decrease in the size of the tumor as measured by imaging studies.

The neoplasm may be a solid tumor, wherein the anti-cancer agent may be a gene therapeutic agent, and wherein an increase in permeability is determined by an increase in an immune response in the microenvironment of the tumor.

The IgE antibody may be an antibody specific to MUC1.

The antibody specific to MUC1 may bind an epitope of MUC1 selected from SEQ ID NO: 5.

The heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

The heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

The antibody specific to MUC1 may be mAb 3C6.hIgE, mAb 4H5.hIgE or a combination thereof.

The neoplasm may be pancreatic cancer, gastric cancer, colorectal cancer, ovarian cancer, breast cancer or lung cancer.

The neoplasm may be in vivo or in vitro.

The increase in permeability around the stroma results in a) an increase in the therapeutic index of the anti-cancer agent; b) amelioration of at least one adverse effect of the anticancer agent; c) reduction in the amount of anti-cancer agent for use in treatment; d) increase in the permeability of tumor stroma; and e) depletion of the tumor stroma.

The anti-cancer agent may be for use before the IgE antibody.

The anticancer agent may be for use simultaneously with the IgE antibody.

The IgE antibody may be specific for an antigen associated with a tumor stroma.

According to another embodiment, there is provided a combination comprising a composition comprising at least one IgE antibody; and at least one chemotherapeutic agent, wherein said combination increases the delivery of the anti-cancer agent to a neoplasm in a subject as compared to the delivery of the anti-cancer agent to the neoplasm when administered alone.

The present invention provides compositions and methods for increasing the delivery of anti-cancer agents to the site of neoplasms, and particularly to solid tumors. In one embodiment, combining an IgE antibody with an anti-cancer agent in accordance with the invention increases the delivery of the anticancer agent to the site of, for example a solid tumor. In one embodiment, combining an IgE antibody with an anti-cancer agent in accordance with the invention potentiates a tumor's responsiveness and sensitivity to the anti-cancer agent.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

DETAILED DESCRIPTION OF THE INVENTION

Figure 1:
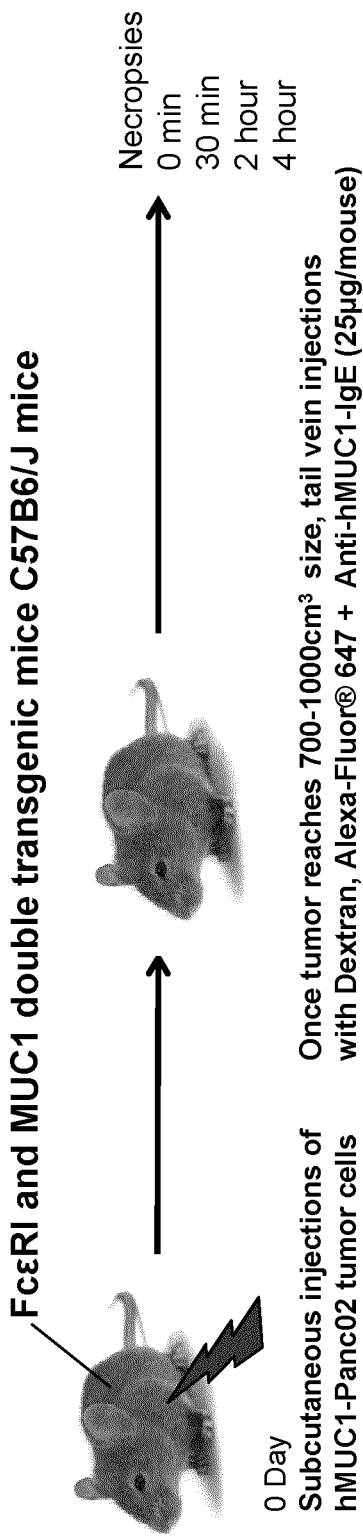
FIG. 1 illustrates an experimental design for testing the method of the present invention.

A description of preferred embodiments of the invention follows.

I. Definitions

The term "composition" as used herein is intended to encompass a product comprising the specified ingredients in the specified amounts, as well as any product which results, directly or indirectly, from combination of the specified ingredients in the specified amounts. Such term in relation to pharmaceutical composition or other compositions in general, is intended to encompass a product comprising the active ingredient(s) and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions or other compositions in general of the present invention encompass any composition made by admixing a compound of the present invention and a pharmaceutically acceptable carrier. By "pharmaceutically acceptable" or "acceptable" it is meant the carrier, diluent or excipient must be compatible with the other ingredients of the formulation and not deleterious to the recipient thereof.

In some embodiments, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the antibody or fragment thereof, preferably in purified form, together with a suitable amount of carrier so as to provide the form for proper administration to the patient. The formulation should suit the mode of administration.

The terms "inhibit", "inhibition" or "inhibiting" as used herein in the context of the invention means to slow, hinder, restrain reduce or prevent. For example, "inhibiting growth" of a tumor cell as that term is used herein means to slow, hinder, restrain, reduce or prevent the tumor cell from growing.

The term "administering" as used herein refers to any action that results in exposing or contacting a composition containing an IgE antibody specific for a cancer antigen, an antigen present in or around a stroma of a tumor, or a combination thereof, alone or in combination with at least one anti-cancer agent. As used herein, administering may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells, or by direct intra-tumoral injection of the IgE antibody specific for a cancer antigen, an antigen present in or around a stroma of a tumor, or a combination thereof with at least one anti-cancer agent individually or in a mixture.

The term "epitope" is intended to mean the portion of an antigen capable of being recognized by and bound by an antibody at one or more of the antibody's binding regions. Epitopes generally comprise chemically active surface groupings of molecules such as amino acids or sugar side chains and have specific three dimensional structure characteristics as well as specific charge characteristics. In one embodiment, an epitope of an antigen is a repetitive epitope. In one embodiment an epitope of an antigen is a non-repetitive epitope.

The terms, "therapeutic IgE antibody" or "IgE antibody" includes but is not limited to an antibody comprising Fc epsilon (ε) constant regions and a variable region comprising at least one antigen binding region specific for an antigen (e.g. a cancer antigen or an antigen present in or around the stroma of a tumor), that can bind to an antigen on a target cell or in circulation to cause a therapeutic effect in a patient. In one embodiment, the antigen is not an allergen or other antigen that is the normal physiological target of unmodified IgE present in the subject. In one embodiment, the therapeutic IgE antibody or IgE antibody is a monoclonal antibody. One class of therapeutic IgE monoclonal antibodies are described in U.S. Ser. No. 13/456,492, incorporated herein by reference.

In another embodiment, the term "therapeutic IgE antibody derivative" or "IgE antibody derivative" refers to derivatives of IgE therapeutic antibodies or IgE antibodies including but not limited to: fragments of IgE antibodies such as F(ab)$_2$, F(ab) and Dab; single chain antibodies representing the reactive portion of the IgE antibody; antigen binding peptides fused to a molecule that mediates an IgE effector function; and mimics of fragments of any of the above. For ease of reference the term "therapeutic IgE antibody" or "IgE antibodies" is used herein to collectively refer to both IgE antibodies and IgE antibody derivatives.

The terms "monoclonal antibody" or "monoclonal antibodies" as used herein refer to a preparation of antibodies of single molecular composition. A monoclonal antibody composition displays a single binding specificity and affinity for a particular epitope. The monoclonal antibodies of the present invention are preferably chimeric, humanized, or fully human in order to bind human Fc epsilon receptors when the subject host is a human. Humanized and fully human antibodies are also useful in reducing immunogenicity toward the murine components of, for example, a chimeric antibody, when the host subject is human. Methods for producing monoclonal antibodies are well known in the art. Therapeutic IgE monoclonal antibodies are described in U.S. Ser. No. 13/456,492, incorporated herein by reference.

The term "antigen binding region" refers to that portion of an IgE antibody which contains the amino acid residues that interact with an antigen and confer on the antibody its specificity and affinity for the antigen. The antibody region includes the "framework" amino acid residues necessary to maintain the proper confirmation of the antigen binding residues.

An "antigen" is a molecule or portion of a molecule capable of being bound by an antibody which is additionally capable of inducing an animal to produce antibody capable of binding to an epitope of that antigen. In one embodiment, the antigen is capable of being bound by an IgE antibody of the invention to form an immune complex that is capable of inducing a specific IgE-mediated immune response to the antigen in a patient capable of mounting such immune response. As used herein, a "patient capable of mounting (the referenced) immune response" is a subject such as a human patient or other animal subject with functional T-cells, mast cells, basophils, eosinophils, monocytes, macrophages and dendritic cells with receptor affinity for the administered IgE antibody of the invention as distinguished from non-human animal models, for example, whose immune systems do not contain Fc epsilon receptors capable of binding human IgE permitting generation of functional T-cells, mast cells, eosinophils and dendritic cells in response to the administered antibody.

The term "anticancer agent" as used herein includes, but is not limited to: anti-neoplastic agents such as chemotherapeutics; immunotherapeutic agents (peptide vaccines etc); radiation therapy; photosensitizers (photodynamic therapy); and gene therapeutic agents such as plasmids and vectors containing immune response modifiers. It is also to be understood that an "agent" may be a single compound or a combination or composition of two or more compounds.

As used herein "anti-neoplastic agents" are drugs that inhibit and combat the development of cancer. Anti-neoplastic agents include but are not limited to chemotherapeutics, monoclonal antibodies, and kinase inhibitors.

The term "immunotherapeutic agents" means immune modulators, cytokines, growth factors, immune modulatory antibodies, vaccines, and immune adjuvants. Examples include IL2, GMCSF, alpha interferon, beta interferon, ipilimumab, bevacizumab, oregovomab, trastuzumab, cetuximab, Sipuleucel T, alpha Dendritic Cells, adoptive T cell therapies, saponins, and TLR agonists (e.g. TLR3 agonist such as polyIC, polyICLC (Hiltonol®); TLR4 agonist), immune homeostatic checkpoint inhibitor such as anti-PD-1 antibody, an anti-PDL-1, an anti-CTLA-4 antibody, or molecular inhibitors of these receptors. Immune homeostatic checkpoint inhibitors are monoclonal antibodies (mAb) directed to immune checkpoint molecules, which are expressed on immune cells and mediate signals to attenuate excessive immune reactions. According to an embodiment, immune homeostasis checkpoint inhibition may be performed with inhibitory monoclonal antibodies directed at the inhibitory immune receptors CTLA-4, PD-1, and PDL-1. According to some embodiments, such inhibitors have emerged as successful treatment approaches for patients with advanced melanoma. According to an embodiment, the immune homeostatic checkpoint inhibitors may be one of an anti-CTLA-4, anti-PD-1, and/or anti-PDL-1 antibody. According to an embodiment, the anti-CTLA-4 antibody may be Ipilimumab or tremelimumab or combinations thereof. According to another embodiment, the anti-PDL-1 antibody may be B7-H1 antibody, BMS-936559 antibody, MPDL3280A (atezolizumab) antibody, MEDI-4736 antibody, MSB0010718C antibody or combinations thereof. According to another embodiment, the anti-PD-1 antibody may be Nivolumab antibody, pembrolizumab antibody, pidilizumab antibody or combinations thereof. In addition, PD-1 may also be targeted with AMP-224, which is a PD-L2-IgG recombinant fusion protein. Additional antagonists of inhibitory pathways in the immune response are being advanced through clinical development. IMP321 is a soluble LAG-3 Ig fusion protein and MHC class II agonist, which is used to increase an immune response to tumors. LAG3 is an immune checkpoint molecule. Lirilumab is an antagonist to the KIR receptor and BMS 986016 is an antagonist of LAG3. A third inhibitory checkpoint pathway is the TIM-3-Galectin-9 pathway that is also a promising target for checkpoint inhibition. RX518 targets and activates the glucocorticoid-induced tumor necrosis factor receptor (GITR), a member of the TNF receptor superfamily that is expressed on the surface of multiple types of immune cells, including regulatory T cells, effector T cells, B cells, natural killer (NK) cells, and activated dendritic cells.

The term "photosensitizers" as used herein means those drugs useful in photodynamic therapy (PDT) that are generally non-toxic, light sensitive compounds that when exposed selectively to light, become toxic to targeted malignant and other diseased cells. Examples of such photosensitizer compounds useful in accordance with the invention include, but are not limited to those found in GB 2442915 and US Pub. No. 2002/0155089.

The term "gene therapeutic agents" as used herein means nucleic acid constructs, administered to patients with the intention of achieving either transient gene expression and translation or integration of the genetic material for longer term expression of the coded gene product often a growth factor and a tumor antigen. Examples include, but are not limited to: the TRICOM vectors described in Garnett et al. (2006) *Curr. Pharm Des.* 12(3):351-61 and adeno-associated vector plasmids (AAV).

As used herein the term "neoplasm" refers to an abnormal growth of cells or tissue and is understood to include benign, i.e., non-cancerous growths, and malignant, i.e., cancerous growths. The term "neoplastic" means of or related to a neoplasm. "Neoplasm" is used interchangeably herein with the term "cancer".

The term "therapeutic index" (TI) as used herein with regard to a chemotherapeutic agent is the ratio $LD_{50}/ED_{50}$. Therapeutic efficacy and possible toxicity of chemotherapeutic compositions can be determined by standard pharmaceutical procedures, in cell cultures or experimental animals (e.g., $ED_{50}$, the dose therapeutically effective in 50% of the population; and $LD_{50}$, the dose lethal to 50% of the population). In one embodiment, the therapeutic index of a chemotherapeutic agent is increased at least about 2-fold, preferably at least about 5-fold, preferably at least about 10 fold or more when co-administered with an IgE antibody in accordance with the invention. In humans therapeutic index is defined in terms of $TD_{50}/ED_{50}$ where $TD_{50}$ is the median toxic dose. Since many anti-neoplastic agents are highly toxic and have narrow therapeutic windows, improving delivery of these agents to the site of pathology while reducing systemic exposure to the agent is a desirable improvement in clinical management that will result in preserved or improved therapeutic efficacy of the agent with reduced toxicity.

The term "increasing the delivery of an anticancer agent" means that the delivery of an anti-cancer agent to the site of a neoplasm such as a solid tumor, has been increased as a result of co-administration of an IgE antibody with an anti-cancer agent in accordance with the invention, as compared to administration of the anticancer agent in the absence of co-administration of an IgE antibody in accordance with the invention.

Comparative data obtained from appropriate assays is used in determining if the therapeutic index has been increased. In one embodiment, the delivery of an anti-neoplastic agent such as a chemotherapeutic agent to a neoplasm is increased as measured by the uptake of polydextrans of different sizes in the stroma. In one embodiment, the delivery of immunotherapeutic agents to a neoplasm is increased as measured by the increased presence of tumor infiltrating lymphocytes in the tumor or stroma. In one embodiment, the delivery of radiation to the tumor is increased as measured by decreased tumor size in imaging studies. In one embodiment, the delivery of photosensitizers to a tumor is increased as is monitored by decreased tumor size in imaging studies. In one embodiment, the delivery of gene therapeutic agents such as plasmids and vectors containing immune response modifiers is increased as is measured by the targeted immune response in the subject.

As used herein, the term "ameliorating at least one adverse effect of an anti-cancer agent" includes: (a) reducing the magnitude and/or duration of at least one adverse effect of an anti-cancer agents; and/or (b) completely eliminating at least one adverse effect of anti-cancer agent; and/or (c) preventing the onset of one or more adverse effect(s) of cancer therapy that would occur without administration of an IgE composition of the invention. Such adverse effects of anti-cancer agents include, but are not limited to: nephrotoxicity, neurotoxicity, ototoxicity, myelosuppression, alopecia, weight loss, vomiting, nausea and immunosuppression. Amelioration of one or more adverse effects of a specific anti-cancer agent can be readily determined by routine experimentation by one of ordinary skill in the art.

As used herein to "potentiate a tumor's responsiveness and sensitivity to an anti-cancer agent" means to render tumor cells more susceptible to treatment by the anti-cancer agent. Tumor cells that have been potentiated to the effects of an anti-cancer agent show a measurably higher decrease in cell viability or tumor size as measured by the standard techniques to measure activity of anti-neoplastic agents in the clinical art. Standard measures of clinical outcome include gross anatomical or radiographic measurement of target lesions, measurements of velocity of growth, measurement of progression free survival and overall survival in human patients and in animal models when compared to cancer cells that have been exposed to the same dosage of the anti-cancer agent in the absence of the potentiating composition (e.g. an IgE antibody) in accordance with the methods of the invention.

As used herein, the term "chemotherapeutic agent" is an agent that is administered to a subject to destroy, or otherwise adversely affect, cancer cells.

As used herein, the term "cancer" is used to mean a condition in which a cell in a patient's body undergoes abnormal, uncontrolled proliferation. The abnormal cell (also referred to herein as a "cancer cell" may proliferate to form a solid tumor, or may proliferate to form a multitude of cells (e.g., leukemia). Note that because cancer is the abnormal, uncontrolled proliferation of a patient's cell, the term does not encompass the normal proliferation of a cell.

A "subject" is preferably a human subject but can also be any mammal, including an animal model, in which modulation of an autoimmune reaction is desired. Mammals of interest include, but are not limited to: rodents, e.g. mice, rats; livestock, e.g. pigs, horses, cows, etc., pets, e.g. dogs, cats; and primates. A subject may also be referred to herein as a "patient". The "subject" will possess functional mast cells, basophils, neutrophils, eosinophils, monocytes, macrophages, dendritic cells, and Langerhans cells. In humans, all of these cells express the high affinity receptor for IgE (FcεRI) for the administered IgE antibody of the invention.

The terms "treatment", "treat" and "treating" encompasses alleviation, cure or prevention of at least one symptom or other aspect of a disorder, disease, illness or other condition (collectively referred to herein as a "condition"), or reduction of severity of the condition, and the like. A composition of the invention need not affect a complete cure, or eradicate every symptom or manifestation of a disease, to constitute a viable therapeutic agent.

As is recognized in the pertinent field, drugs employed as therapeutic agents may reduce the severity of a given disease state, but need not abolish every manifestation of the disease to be regarded as useful therapeutic agents. Beneficial or desired clinical results include, but are not limited to, alleviation of symptoms, diminishment of extent of disease, stabilization (i.e., not worsening) of disease, delay or slowing of disease progression, amelioration or palliation of the disease state, remission (whether partial or total, whether detectable or undetectable) and prevention of relapse or recurrence of disease. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient.

"Treatment" can also mean prolonging survival as compared to expected survival if not receiving treatment. In one embodiment, an indication that a therapeutically effective amount of a composition has been administered to the patient is a sustained improvement over baseline of an indicator that reflects the severity of the particular disorder.

By a "therapeutically effective amount" of a composition of the invention is meant an amount of the composition which confers a therapeutic effect on the treated subject, at a reasonable benefit/risk ratio applicable to any medical treatment. The therapeutic effect is sufficient to "treat" the patient as that term is used herein.

As used herein, the terms "co-administration" or administration "in combination" refers to administering to a subject, at least one anti-cancer agent in combination with at least one IgE antibody. The anti-cancer agent and IgE antibody can be administered at the same time, separately, or sequentially, according to the methods disclosed herein.

The phrase "stroma-modulating amount of an IgE antibody" as used herein means that amount of IgE antibody that is sufficient to cause a reaction in the tumor such as, for example, the depletion of the tumor stroma and/or an increase in stromal permeability, without causing significant systemic immune reactions.

The phrase "effective amount of an IgE antibody" as used herein means that amount of IgE antibody that is sufficient to cause a reaction in the tumor such as, for example, the depletion of the tumor stroma and/or an increase in stromal permeability, without causing significant systemic immune reactions.

"Deplete", depleting" or "depletion" of the tumor stroma as that phrase is used herein includes any reduction in the size of the tumor stroma as compared to the tumor stroma prior to contact with an therapeutic IgE antibody in accordance with the invention and modification of the nurturing capacity of the stroma such that the interaction of the malignant cells with the stroma and administered antineoplastics is fundamentally changed. Changes may include increased leakage from the cells in the tumor stroma resulting in accumulation of anti-neoplastics in the third space of the tumor; but also could include modification to the stromal architecture, destruction of fibrous scaffolding, potentiating of infiltrating tumor targeting host response.

The term "increase in stromal permeability" as used herein includes changes in the vascular leakage into the tumor space and, for example, the ability of T cells to infiltrate the tumor microenvironment. For example, in a tumor model, a syngeneic pancreatic cancer orthotopically placed into a mouse or a sample subcutaneous tumor growth model, one can image dextran of various molecular weights (MW) before and after treatment with the invention and demonstrate changes in the vascular leakage into the tumor space by using multiple cutoffs for the labeled dextran one can characterize the magnitude and MW size restrictions of the effect. In another example one can vaccinate an animal and demonstrate induction of tumor specific T cells; one can then either remove those T cells and culture them as an autologous T-cell therapy and infuse them with or without IgE treatment and demonstrate changes in the ability of these T cells to home to the tumor. This can also be done using an ex vivo T cell therapy approach or simply empirically in the vaccinated animal itself. The readout is the T cell infiltrate and ultimately survival of the animal by labeling exogenous cells imaging modalities might be employed.

The "tumor stroma" as that term is used herein refers to the fibrous tissue that surrounds cancer cells. It is generally formed from fibroblasts, adipocytes, inflammatory cells, and vascular cells and is further characterized by the presence of myofibroblasts.

Before describing the present invention in detail, a number of terms will be defined. As used herein, the singular forms "a", "an", and "the" include plural referents unless the context clearly dictates otherwise.

It is noted that terms like "preferably", "commonly", and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

II. Compositions and Methods

In accordance with one embodiment, compositions and methods of the present invention can be used to increase the delivery of an anti-cancer agent to cancer cells, particularly cancer cells associated with a solid tumor, wherein the method comprises the step of co-administering to a subject, a therapeutically effective amount of at least one IgE antibody and at least one anti-cancer agent. The anti-cancer agent and IgE antibody can be co-administered simultaneously, in either separate or combined formulations, or sequentially at different times, and in any order, separated by minutes, hours, days or weeks, but in some way act together to provide the desired therapeutic response.

The delivery of the anti-cancer agent to a neoplasm such as a solid tumor, is increased as compared to the delivery of the same anti-cancer agent in the absence of co-administration of a IgE antibody in accordance with the invention. In one embodiment, the delivery of an anti-neoplastic agent such as a chemotherapeutic agent to a tumor is increased as measured by the uptake of polydextrans of different sizes in the stroma. In one embodiment, the delivery of immunotherapeutic agents to a tumor is increased as measured by the increased presence of tumor infiltrating lymphocytes in the tumor or stroma. In one embodiment, the delivery of radiation to the tumor is increased as measured by decreased tumor size in imaging studies. In one embodiment, the delivery of photosensitizers to a tumor is increased as is monitored by decreased tumor size in imaging studies. In one embodiment, the delivery of gene therapeutic agents such as plasmids and vectors containing immune response modifiers to a neoplasm is increased as measured by immune response.

All tumors have stroma and require stroma for nutritional support and for the removal of waste products. In the case of leukemias, blood plasma serves as stroma, although an additional stromal response, angiogenesis, may develop in the bone marrow. When tumors grow in body cavities, a plasma exudate (e.g. ascites) provides stroma. In solid tumors, stroma includes connective tissue, blood vessels, and, very often, inflammatory cells, all of which are interposed between the malignant cells and normal host tissues. In all tumors, stroma is largely a product of the host and is induced as the result of tumor cell-host interactions. Solid tumors, regardless of their type or cellular origin, require stroma if they are to grow beyond a minimal size of 1 to 2 mm. The stroma of solid tumors may also limit the influx of inflammatory cells or may limit the egress of tumor cells (invasion). Stroma, therefore, at once provides a lifeline that is necessary for tumor growth and imposes a barrier that inhibits and may regulate interchange of fluids, gases, and cells.

The singular importance of new blood vessel formation to tumor survival and growth has rightly led to an emphasis on tumor angiogenesis; however, this emphasis has been accompanied by an unfortunate tendency to undervalue other tumor stromal components. Blood vessels are only one component of tumor stroma. In fact, in many tumors, the bulk of stroma comprises interstitial connective tissue, and blood vessels are only a minor component of the stromal mass. For the most part, tumor stroma is formed by elements that are derived from the circulating blood and from adjacent host connective tissues.

Therefore, in solid tumors the stroma can act as both a source of nutrition and a barrier, but the stroma intermingles with the tumor and is included to some degree in the measurements of tumors removed from normal tissue and in imaging. Without being limited to any particular theory, it is believed that the IgE antibodies used in accordance with the invention modifies the fundamental biological character of the stromal tissue and creates a modified inflammatory environment that can facilitate delivery of cells and chemicals to this space with increased delivery per unit dose of anticancer treatment. Quantification of effects of IgE on the tumor and surrounding stroma can be standard measures of tumor size as used in the art, but also comparative morphology of the cellular architecture, measurement of local cytokines, chemokines, and mediators produced in the tumor microenvironment.

The combination treatment regimen of the invention provides many benefits that enhance anti-cancer treatment regimens. One such benefit includes reducing the amount of anti-cancer agent needed to treat disease. In one embodiment, combining an IgE antibody with an anticancer agent in accordance with the invention ameliorates at least one adverse effect of the anti-cancer agent. In one embodiment combining an IgE antibody with an anticancer agent that is a chemotherapeutic agent in accordance with the invention increases the therapeutic index of the chemotherapeutic agent. In one embodiment, combining an IgE antibody with an anticancer agent in accordance with the invention modulates the stroma surrounding a tumor, for example by depleting tumor stroma. In one embodiment, combining an IgE antibody with an anticancer agent in accordance with the invention increases the permeability of the stroma surrounding a tumor. Other advantages provided by the compositions and methods of the invention in anti-cancer treatment regimens will be apparent to those skilled in the art.

In one embodiment, the IgE antibody is specific for an antigen associated with a tumor's microenvironment, including antigens found in and around the tumor stroma. Target antigens associated with the tumor stroma may be of normal or neoplastic origin. Tumors associated with, intractable cancers such as pancreatic cancer, gastric cancer, colorectal cancer, and lung cancer are known to be rich in stroma.

For example, collagens, which are present in normal living organisms are well developed in inflamed tissues and tumor stroma tissues. Type IV collagen is abundant around tumor blood vessels, whereas type I and type III collagens are prevalent between tumor cells and tumor blood vessels. Elastin, proteoglycan, fibronectin, laminin are also present in tumor stroma. These proteins provide targets for IgE in accordance with the invention.

In addition, in the tumor microenvironment antigens are induced or upregulated on stroma cells that can be targeted by IgE antibody in accordance with the invention. Such targets include, but are not limited to cancer-associated fibroblasts (CAFs), tumor endothelial cells (TEC) and tumor-associated macrophages (TAM). Examples of cancer-associated fibroblasts (CAFs) include but are not limited to: carbonic anhydrase IX (CAIX); fibroblast activation protein alpha (FAPα); and matrix metalloproteinases (MMPs) including MMP-2 and MMP-9. Examples of Tumor endothelial cell (TECs) target antigens include, but are not limited to vascular endothelial growth factor (VEGF) including VEGFR-1, 2, and 3; CD-105 (endoglin), tumor endothelia markers (TEMs) including TEM1 and TEM8; MMP-2; Survivin; and prostate-specific membrane antigen (PMSA). Examples of tumor associated macrophage antigens include, but are not limited to: CD105, MMP-9; VEGFR-1, 2, 3 and TEM8.

In one embodiment, the IgE antibody may be specific for target antigens located on tumor cells, for example, VEGFR-2, MMPs, Survivin, TEM8 and PMSA. In one embodiment, the IgE antibody is specific for any type of cancer antigen known in the art. The cancer antigen may be an epithelial cancer antigen, (e.g., breast, gastrointestinal, lung), a prostate specific cancer antigen (PSA) or prostate specific membrane antigen (PSMA), a bladder cancer antigen, a lung (e.g., small cell lung) cancer antigen, a colon cancer antigen, an ovarian cancer antigen, a brain cancer antigen, a gastric cancer antigen, a renal cell carcinoma antigen, a pancreatic cancer antigen, a liver cancer antigen, an esophageal cancer antigen, a head and neck cancer antigen, or a colorectal cancer antigen. A cancer antigen can also be a lymphoma antigen (e.g., non-Hodgkin's lymphoma or Hodgkin's lymphoma), a B-cell lymphoma cancer antigen, a leukemia antigen, a myeloma (i.e., multiple myeloma or plasma cell myeloma) antigen, an acute lymphoblastic leukemia antigen, a chronic myeloid leukemia antigen, or an acute myelogenous leukemia antigen.

Other cancer antigens include but are not limited to mucin-1 protein or peptide (MUC-1) that is found on all human adenocarcinomas: pancreas, colon, breast, ovarian, lung, prostate, head and neck, including multiple myelomas and some B cell lymphomas; mutated B-Raf antigen, which is associated with melanoma and colon cancer; human epidermal growth factor receptor-2 (HER-2/neu) antigen; epidermal growth factor receptor (EGFR) antigen associated lung cancer, head and neck cancer, colon cancer, colorectal cancer, breast cancer, prostate cancer, gastric cancer, ovarian cancer, brain cancer and bladder cancer; prostate-specific antigen (PSA) and/or prostate-specific membrane antigen (PSMA) that are prevalently expressed in androgen-independent prostate cancers; is gp-100 (Glycoprotein 100) associated with melanoma carcinoembryonic (CEA) antigen; carbohydrate antigen 19.9 (CA 19.9) related to the Lewis A blood group substance and is associated with colorectal cancers; and a melanoma cancer antigen such as MART-1.

Therefore, in embodiments, the IgE antibody may be any suitable antibody. According to another embodiment, the IgE antibody may be for example mAb 3C6.hIgE, mAb 4H5.hIgE. According to another embodiment, the IgE antibody may be a chimeric monoclonal antibody, a humanized monoclonal antibody or a fully human monoclonal antibody.

Methods for raising antibodies, such as murine antibodies to an antigen, and for determining if a selected antibody binds to a unique antigen epitope are well known in the art.

Screening for the desired antibody can be accomplished by techniques known in the art, e.g., radioimmunoassay, ELISA (enzyme-linked immunosorbant assay), "sandwich" immunoassays, immunoradiometric assays, gel diffusion precipitin reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. Many means are known in the art for detecting binding in an immunoassay and are within the scope of the present invention.

For preparation of monoclonal antibodies, any technique that provides for the production of antibody molecules by continuous cell lines in culture may be used (see, e.g., Antibodies—A Laboratory Manual, Harlow and Lane, eds., Cold Spring Harbor Laboratory Press: Cold Spring Harbor, N.Y., 1988). These include but are not limited to the hybridoma technique originally developed by Kohler and Milstein (1975, *Nature* 256:495-497), as well as the trioma technique, the human B-cell hybridoma technique (Kozbor et al., 1983, *Immunology Today*, 4:72), and the EBV-hybridoma technique to produce human monoclonal antibodies (Cole et al., 1985, in Monoclonal Antibodies and Cancer Therapy, Alan R. Liss, Inc., pp. 77-96). In an additional embodiment of the invention, monoclonal antibodies can be produced in germ-free animals utilizing recent technology (PCT/US90/02545). According to the invention, human antibodies may be used and can be obtained by using human hybridomas (Cote et al., 1983, *Proc. Natl. Acad. Sci. U.S.A.*, 80:2026-2030) or by transforming human B cells with EBV virus in vitro (Cole et al., 1985, in Monoclonal Antibodies and Cancer Therapy, Alan R. Liss, pp. 77-96). In fact, according to the invention, techniques developed for the production of "chimeric antibodies" (Morrison et al., 1984, *J. Bacteriol.* 159: 870; Neuberger et al., 1984, *Nature* 312:604-608; Takeda et al., 1985, *Nature* 314: 452-454) by splicing the genes from a mouse antibody molecule specific for a polypeptide together with genes from a human antibody molecule of appropriate biological activity can be used; such antibodies are within the scope of this invention.

In one embodiment, the antibody used in the invention is an IgE monoclonal antibody comprising a nucleic acid sequence selected from a heavy chain variable region encoded by a nucleic acid sequence comprising SEQ ID NO: 1; a light chain variable region encoded by a nucleic acid sequence comprising SEQ ID NO: 2 and any combination thereof and wherein the heavy and light chain is grafted onto human epsilon heavy chain and kappa light chain genes, respectively.

In one embodiment the antibody used in the invention is an IgE monoclonal antibody comprising a nucleic acid sequence selected from a heavy chain variable region encoded by the nucleic acid of SEQ ID NO: 3; a light chain variable region encoded by the nucleic acid of SEQ ID NO: 4 and any combination thereof and wherein the heavy and light chain is grafted onto human epsilon heavy chain and kappa light chain genes, respectively.

In one embodiment, the invention provides a monoclonal antibody, 3C6.hIgE, comprising variable regions of the light and heavy chain of IgG cloned from the VU-3C6 hybridoma, and grafted onto human Ig kappa light chain and epsilon heavy chain genes, respectively. VU-3C6 targets human mucin 1 (hMUC1), a hypoglycosylated form of mucin overexpressed on tumors arising from glandular epithelium. In one embodiment, the invention comprises the IgE antibody, 4H5.hIgE, which is specific to an isoform of MUC1 different from the MUC1 isoform that 3C6.hIgE is specific to.

In one embodiment, the antibody of the invention is the monoclonal antibody 3C6.hIgE comprising a heavy chain variable region encoded by a nucleic acid sequence comprising SEQ ID NO: 1; a light chain variable region encoded by a nucleic acid sequence comprising SEQ ID NO: 2.

In one embodiment the antibody of the invention is the monoclonal antibody 4H5.hIgE. The antibody 4H5.hIgE has a heavy chain variable region encoded by the nucleic acid of SEQ ID NO: 3 and a light chain variable region encoded by the nucleic acid of SEQ ID NO: 4 and grafted onto human Ig kappa light chain and epsilon heavy chain genes.

In one embodiment, the therapeutic monoclonal antibody specific for a tumor associated antigen is an IgE monoclonal antibody specific for an epitope of MUC1. In one embodiment, the antibody of the invention is specific for the epitope of MUC1 comprising amino acids STAPPAHGVTSAP-DTRPAPG [SEQ ID NO: 5] of MUC1. The exact epitope lies in one of the 20 amino acid repeats that characterize the external domain of MUC1. In one embodiment, the antibody of the invention is capable of binding MUC1 at the epitope defined at STAPPAHGVTSAPDTRPAPG [SEQ ID NO: 5].

In one embodiment, therapeutic monoclonal antibodies specific for a tumor associated antigen in accordance with the present invention are expressed by a positive transfectoma which is identified by enzyme-linked immunosorbent assay (ELISA) and Western Blot. The positive transfectoma will be cloned by limited dilution for highest productivity and selected for antibody production. As used herein a "transfectoma" includes recombinant eukaryotic host cells expressing the antibody, such as Chinese hamster ovary (CHO) cells and NS/O myeloma cells. Such transfectoma methodology is well known in the art (Morrison, S. (1985) *Science*, 229:1202). Previously published methodology used to generate mouse/human chimeric or humanized antibodies has yielded the successful production of various human chimeric antibodies or antibody fusion proteins (Helguera G, Penichet M L., *Methods Mol. Med.* (2005) 109:347-74).

In general, chimeric mouse-human monoclonal antibodies (i.e., chimeric antibodies) can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted. (See Robinson et al., International Patent Publication PCT/US86/02269, Akira, et al., European Patent Application 184,187; Taniguchi, M., European Patent Application 171, 496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988 *Science*, 240:1041-1043); Liu et al. (1987) *PNAS*, 84:3439-3443; Liu et al., 1987, *J. Immunol.*, 139:3521-3526; Sun et al. (1987) *PNAS*, 84:214-218; Nishimura et al., 1987, *Canc. Res.*, 47:999-1005; Wood et al. (1985) *Nature*, 314:446-449; and Shaw et al., 1988, *J. Natl Cancer Inst.*, 80:1553-1559).

The chimeric antibody can be further humanized by replacing sequences of the Fv variable region which are not directly involved in antigen binding with equivalent sequences from human Fv variable regions. General reviews of humanized chimeric antibodies are provided by Morrison, S. L., 1985, *Science*, 229:1202-1207 and by Oi et al., 1986, *BioTechniques*, 4:214. Those methods include isolating, manipulating, and expressing the nucleic acid sequences that encode all or part of immunoglobulin Fv variable regions from at least one of a heavy or light chain. Sources of such nucleic acid are well known to those skilled in the art and, for example, may be obtained from 7E3, an anti-GPII$_b$III$_a$ antibody producing hybridoma. The recombinant DNA encoding the chimeric antibody, or fragment thereof, can then be cloned into an appropriate expression vector. Suitable humanized antibodies can alternatively be produced by CDR substitution (U.S. Pat. No. 5,225,539; Jones et al. 1986 Nature, 321:552-525; Verhoeyan et al. 1988 Science, 239:1534; and Beidler et al. 1988 J. Immunol., 141:4053-4060).

Exemplary anti-neoplastic agents of the present invention can include one or more agents selected from the group consisting of nitrogen mustards (e.g., cyclophosphamide and ifosfamide), aziridines (e.g., thiotepa), alkyl sulfonates (e.g., busulfan), nitrosoureas (e.g., carmustine and streptozocin), platinum complexes (e.g., carboplatin and cisplatin), non-classical alkylating agents (e.g., dacarbazine and temozolomide), folate analogs (e.g., methotrexate), purine analogs (e.g., fludarabine and mercaptopurine), adenosine analogs (e.g., cladribine and pentostatin), pyrimidine analogs (e.g., fluorouracil (alone or in combination with leucovorin) and gemcitabine), substituted ureas (e.g., hydroxyurea), antitumor antibiotics (e.g., bleomycin and doxorubicin), epipodo-phyllotoxins (e.g., etoposide and teniposide), microtubule agents (e.g., docetaxel and paclitaxel), camptothecin analogs (e.g., irinotecan and topotecan), enzymes (e.g., asparaginase), cytokines (e.g., interleukin-2 and interferon-.alpha.), monoclonal antibodies (e.g., trastuzumab and bevacizumab), recombinant toxins and immunotoxins (e.g., recombinant cholera toxin-B and TP-38), cancer gene therapies, physical therapies (e.g., hyperthermia, radiation therapy, and surgery) and cancer vaccines (e.g., vaccine against telomerase).

Anti-neoplastic agents may also be categorized by their mechanism of action into, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors. Preferred dosages of the chemotherapeutic agents are consistent with currently prescribed dosages. In accordance with the methods of the invention the dosages of chemotherapeutic agents may be lower than those previously necessary due to co-administration of the IgE in accordance with the invention.

Additional anti-neoplastic agents can also be compounds and antisense RNA, RNAi or other polynucleotides to inhibit the expression of the cellular components that contribute to unwanted cellular proliferation that are targets of conventional chemotherapy. Such targets are, merely to illustrate, growth factors, growth factor receptors, cell cycle regulatory proteins, transcription factors, or signal transduction kinases.

The compositions and methods according to the invention are useful for providing a therapeutic benefit to patients suffering from various types of cancer. Such cancers include but are not limited to pancreatic cancer, gastric cancer (cancer of the gastrointestinal tract), colorectal cancer, and lung cancer. Other types of cancers that may be treated by the methods of the invention include but are not limited to: osteosarcoma, esophageal cancer, lung cancer, mesothelioma, liver cancer, gastric cancer, pancreatic cancer, colorectal cancer, rectal cancer, colic cancer, ureteral tumor, brain tumor, gallbladder cancer, cholangioma, bile duct cancer, renal cancer, breast cancer, urinary bladder cancer, ovarian cancer, uterocervical cancer, prostatic cancer, thyroid cancer, testicle tumor, Kaposi's sarcoma, maxillary cancer, tongue cancer, lip cancer, oral cancer, laryngeal cancer, pharyngeal cancer, myosarcoma, skin cancer and the like.

In one embodiment compositions of the invention are useful in instances where chemotherapy is indicated including induction chemotherapy, primary (neoadjuvant) chemotherapy, and adjuvant chemotherapy. In addition, chemotherapy frequently is indicated as adjuvants to surgery in the treatment of cancer. The goal of chemotherapy in the adjuvant setting is to reduce the risk of recurrence and enhance disease-free survival when the primary tumor has been controlled. Chemotherapy is utilized as a treatment adjuvant for colon, lung, and breast cancer, frequently when the disease is metastatic. Compounds of the invention therefore are useful following surgery in the treatment of cancer in combination with radio- and/or chemotherapy.

In another embodiment, the present invention provides methods for ameliorating at least one adverse effect of an anti-cancer agent, wherein the method comprises the step of co-administering to a subject, a therapeutically effective amount of at least one IgE antibody and at least one anti-cancer agent. Adverse effects ameliorated by the compositions and methods of the invention include, but are not limited to: nephrotoxicity, neurotoxicity, ototoxicity, myelosuppression, alopecia, weight loss, vomiting, nausea and immunosuppression.

In one embodiment the compositions and methods of the invention potentiate a tumor's responsiveness and sensitivity to an anti-cancer agent when the agent is given in combination with an IgE antibody of the invention. In one embodiment the compositions and methods of the invention inhibit or reduce the growth of tumors in vivo and in vitro. As used herein "inhibiting" or "reducing" the growth of a tumor means to slow down, to decrease, or, for example, to stop the amount of cell proliferation, as measured using methods known to those of ordinary skill in the art, by, for example, 10%, 20%, 30%, 40%, 50%, 60%, 70%, 80%, 90%, 95%, or 100%, when compared to proliferating cells that are not subjected to the methods and compositions of the present application. In one embodiment the compositions and methods of the invention decrease the size of tumors in vivo and in vitro. As used herein "decreasing the size" of tumor means to reduce overall tumor size, volume or bulk by, for example, 10%, 20%, 30%, 40%, 50%, 60%, 70%, 80%, 90%, 95%, or 100%, as measured using known methods such as imaging studies, when compared to tumors that are not subjected to the methods and compositions of the present application.

The amount of IgE antibody and therapeutically effective amount of an anti-cancer agent which will be effective in accordance with the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems. The selected dosage level will also depend upon a variety of factors including the activity of the particular compound employed, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

As used herein, "administering" to a subject refers to any action that results in exposing or contacting a composition containing an IgE antibody and/or an anti-cancer agent with a pre-determined cell, cells, or tissue, including tumor stroma. As used herein, "administering" may be conducted in vivo, in vitro, or ex vivo. For example, a composition may be administered by injection or through an endoscope. Administering also includes the direct application to cells of a composition according to the present invention. For example, during the course of surgery, tumor cells may be exposed. In accordance with an embodiment of the invention, these exposed cells (or tumors) may be exposed directly to a composition of the present invention, e.g., by washing or irrigating the surgical site and/or the cells.

In accordance with the methods of the invention, the IgE antibody and the anti-cancer agent are administered simultaneously, in either separate or combined formulations, or sequentially at different times separated by minutes, hours or days, but in some way act together to provide the desired therapeutic response.

In some embodiments of the invention, one or more anti-cancer agents are administered to a subject at any time during a period of time ranging from two weeks, one week, 48 hours, 36 hours, 24 hours, 18 hours, 12 hours, 10 hours, 8 hours, 6 hours, 4 hours, 1 hour, 30 minutes, 5 minutes or 1 minute prior to, or after, administration of one or more IgE antibodies to the subject. In some embodiments of the invention, one or more anti-cancer agents are administered to a subject concurrently with administration of one or more IgE antibodies to the subject in a single composition where appropriate or in separate compositions.

In one embodiment, the IgE antibody is conjugated to, for example, a chemotherapeutic agent using known techniques. Tumor-directed delivery of such conjugates further enhances the therapeutic benefit by minimizing potential nonspecific toxicities which can result chemotherapy.

In accordance with a method of the invention compositions comprising the IgE antibody and compositions comprising, for example, a chemotherapeutic agent (whether the same or different) may be administered to the patient by any immunologically suitable route. For example, the IgE antibody may be introduced into the patient by an intravenous, subcutaneous, intraperitoneal, intrathecal, intravesical, intradermal, intramuscular, or intralymphatic routes. The composition may be in solution, tablet, aerosol, or multiphase formulation forms. Liposomes, long-circulating liposomes, immunoliposomes, biodegradable microspheres, micelles, or the like may also be used as a carrier, vehicle, or delivery system. Furthermore, using ex vivo procedures well known in the art, blood or serum from the patient may be removed from the patient; optionally, it may be desirable to purify the antigen in the patient's blood; the blood or serum may then be mixed with a composition according to the invention; and the treated blood or serum is returned to the patient. The invention should not be limited to any particular method of introducing the compositions into the patient.

Administration may be once, more than once, and over a prolonged period. In one embodiment, the combination treatment regimen in accordance with the invention may be administered at least one per day, at least once per week, at least once per every two weeks, to at least once per every 4 weeks to at least once per every 6 weeks to at least once per every 8 weeks to at least once per every 10 weeks to at least once to every 14 weeks to at least once to every 16 weeks to at least once to every 18 week. Actual methods and protocols for administering pharmaceutical compositions, including dilution techniques for injections of the present compositions, are well known or will be apparent to one skilled in the art.

In general, the therapeutically effective amount of the IgE antibody administered will be in the range of about 0.001 to about 50 mg/kg; preferably about 0.005 to 25 mg/kg, preferably about 0.005 to 20 mg, preferably about 0.005 to 15 mg/kg, preferably about 0.005 to about 10 mg/kg, preferably about 0.005 to 5 mg/kg, preferably about 0.005 to 1 mg/kg, of patient body weight, whether by one or more administrations, administered daily, for example. However, other dosage regimens may be useful. The progress of this therapy is easily monitored by conventional techniques. In one preferred embodiment the IgE antibody is administered intravenously at a concentration of 0.010 to 0.1 mg/ml at a rate of 1 to 4 ml/min for 30 minutes.

In one embodiment the amount of IgE antibody administered via an infusion or injection, such as about 1 µg of IgE which preferably achieves a serum concentration of about 1 ng/ml. In one embodiment the amount of IgE administered ranges from picograms/kg to about 100 µg per kg.

The chemotherapeutic agents herein are typically administered following dosages and routes of administration used in current clinical practice. For example, 5-fluorouracil (5-FU), Adrucil® is in clinical use for the treatment of breast cancer, gastrointestinal cancers, including anal, esophageal, pancreas and gastric cancers, head and neck cancer, liver cancer, and ovarian cancer, and is typically administered intravenously as an injection, a bolus injection or continuous intravenous infusion. The amount of time and schedule varies depending on the type and stage of cancer, the treatment history and overall condition of patient, and other factors typically considered by practicing physicians. Preferably Society of Clinical Oncology Clinical Practice Guidelines are followed with regard to administration of antineoplastics including chemotherapeutics.

Preferably, the therapeutic compositions of the invention further comprise a pharmaceutically acceptable carrier. By "pharmaceutically acceptable carrier" is meant a carrier that is physiologically acceptable to the administered patient. One exemplary pharmaceutically acceptable carrier is physiological saline. Other pharmaceutically-acceptable carriers and their formulations are well-known and generally described in, for example, *Remington's Pharmaceutical Sciences* (18th Edition, ed. A. Gennaro, Mack Publishing Co., Easton, Pa., 1990).

Formulations, dosages and treatment protocols used to administer the compositions of the present invention will vary depending on the type and stage of cancer, and other factors typically considered in clinical practice, and can be readily determined by those skilled in the art. Therapeutic formulations of IgE antibodies alone or in combination with chemotherapeutic agents are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions.

Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation may also contain more than one active compound as necessary for the particular indication being treated, preferably those with complementary activities that do not adversely affect each other. For example, it may be desirable to further provide an immunosuppressive agent. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacrylate) microcapsule, respectively, in colloidal drug delivery systems (for example, liposomes, albumin microspheres, microemulsions, nano-particles and nanocapsules) or in macroemulsions.

The formulations to be used for in vivo administration are sterile. This is readily accomplished by filtration through sterile filtration membranes. Sustained-release preparations may be prepared. Suitable examples of sustained-release preparations include semipermeable matrices of solid hydrophobic polymers containing the antibody variant, which matrices are in the form of shaped articles, e.g., films, or microcapsule.

III. Additional Embodiments

While not being limited to any particular scientific theory, it is believed that IgE antibody is capable of modulating the tumor microenvironment including, but not limited to, increasing stroma permeability and/or depleting the stroma surrounding a tumor. Reducing stroma size and/or increasing stroma permeability has been shown to enhance the efficacy of chemotherapy and/or radiation therapy in the treatment of tumors and thereby reduce the amount of chemotherapy and/or radiation needed to effectively treat disease. While not being limited to any theory, it is believed that stroma modulating amounts of IgE antibodies of the invention are capable of directing hypersensitivity reactions by binding antigens that are on the tumor or in the vicinity of the tumor and the tumor's microenvironment, such as the tumor stroma, and bringing effector cells including mast cells, basophils, macrophages and eosinophils to the site of a tumor inducing a local allergic inflammatory reaction with local cellular activation in the absence of systemic hypersensitivity and/or anaphylaxis in a subject.

Therefore, in one embodiment, the invention also provides a method of modulating the stroma around a tumor comprising the steps of contacting the tumor stroma with a stroma-modulating (i.e. an effective) amount of at least one IgE antibody. As used herein the phrase "contacting the tumor stroma" means that the IgE antibody is present sufficiently close to the tumor and tumor stroma so as to exert its stroma-modulating effects in the tumor microenvironment thereby causing depletion of the stroma, increased permeability of the stroma or both. In one embodiment the tumor is also contacted with an anti-cancer agent such as an anti-neoplastic agent, radiation, immunotherapeutic agents, photosensitizers, or gene therapeutic agents, after the IgE antibody is contacted with the tumor and even more preferably during a period of time in which stroma depletion or stroma permeability is maximized as a result of being contacted with the IgE antibody.

In one embodiment, the anti-cancer agent is administered during the period of time that stroma depletion and/or permeability is maximized after contact with a stroma-modulating (i.e. an effective) amount of an IgE antibody. In one embodiment, stroma depletion and/or stroma permeability is maximized in the range of 2 to 6 days after administration of a stroma-modulating (i.e. an effective) amount of an IgE antibody, and preferably in the range of 3-4 days after administration of a stroma-modulating (i.e. an effective) amount of an IgE antibody.

In another embodiment the tumor may be observed and tumor specific IgE treatment or control IgE treatment only administered after the tumor has become visible. The animal would then be treated several hours to several days following the IgE administration with specific antineoplastic agents. In some animals the effect of the IgE treatment on tumor stroma will be measured directly prior to anti-neoplastic therapy while in other animals the treatments will be administered and the clinical outcomes in terms of response to antineoplastic as measured by quantitative tumor growth over time and survival will be compared between the tumor antigen specific IgE treated animals and non-specific IgE or no antibody controls.

In other embodiments, the present invention also encompasses the corresponding use of a therapeutically effective amount of at least one IgE antibody specific for a cancer antigen, an antigen present in or around a stroma of a tumor, or a combination thereof and at least one anti-cancer agent to increase the delivery of an anti-cancer agent to a tumor in a subject in need thereof, and/or to modulate the stroma around a solid tumor in a subject in need thereof, and/or to increase the permeability of the stroma around a solid tumor in a subject in need thereof, and/or to potentiate a tumor's susceptibility to an anti-cancer agent in a subject in need thereof.

According to other embodiments, the present invention also encompasses corresponding compositions for use in increasing the delivery of the anti-cancer agent to a neoplasm in a subject in need thereof, and/or for use in inhibiting the growth of a tumor in a subject in need thereof, and/or for use in increasing the delivery of an anti-cancer agent to a tumor in a subject in need thereof, and/or for use in modulating a stroma around a solid tumor in a subject in need thereof, and/or for use in increasing the permeability of a stroma around a solid tumor in a subject in need thereof, and/or composition for use in potentiating a tumor's susceptibility to an anti-cancer agent in a subject in need thereof, the compositions may comprise a therapeutically effective amount of at least one IgE antibody specific for a cancer antigen, an antigen present in or around a stroma of a tumor, or a combination thereof and at least one anti-cancer agent.

According to other embodiments, the present invention also encompasses corresponding kits for use in increasing the delivery of the anti-cancer agent to a neoplasm in a subject in need thereof, and/or for use in inhibiting the growth of a tumor in a subject in need thereof, and/or for use in increasing the delivery of an anti-cancer agent to a tumor in a subject in need thereof, and/or for use in modulating a stroma around a solid tumor in a subject in need thereof, and/or for use in increasing the permeability of a stroma around a solid tumor in a subject in need thereof, and/or composition for use in potentiating a tumor's susceptibility to an anti-cancer agent in a subject in need thereof, the kit may comprise a therapeutically effective amount of at least one IgE antibody specific for a cancer antigen, an antigen present in or around a stroma of a tumor, or a combination thereof; at least one anti-cancer agent; and instructions on how to use the kit.

According to some of these embodiments of uses, compositions and/or kits, the IgE antibody may be specific to a cancer antigen or an antigen associated with a neoplasm's microenvironment.

According to some of these embodiments of uses, compositions and/or kits, the anti-cancer agent may be selected from: anti-neoplastic agents, immunotherapeutic agents, radiation, photosensitizers, gene therapeutic agents and combinations thereof.

According to some of these embodiments of uses, compositions and/or kits, the IgE antibody and the anti-cancer agent may be administered simultaneously or sequentially.

According to some of these embodiments of uses, compositions and/or kits, the IgE antibody may be administered simultaneously and in the same composition as the anti-cancer agent wherein the anti-cancer agent is selected from anti-neoplastic agents, immunotherapeutic agents, photosensitizers, or gene therapeutic agents.

According to some of these embodiments of uses, compositions and/or kits, the IgE antibody may be conjugated to the anti-cancer agent.

According to some of these embodiments of uses, compositions and/or kits, the IgE antibody and the anti-cancer agent may be administered sequentially.

According to some of these embodiments of uses, compositions and/or kits, the IgE antibody and the anti-cancer agent may be administered sequentially, wherein the IgE antibody may be administered at least about 1 minute to about 2 weeks prior to, or after, administration of the anti-cancer agent.

According to some of these embodiments of uses, compositions and/or kits, the neoplasm may be a solid tumor, wherein the anti-cancer agent is an anti-neoplastic agent, and wherein increased delivery of the anti-neoplastic agent to the tumor is measured by an increase in the uptake of polydextrans of different size in the tumor or tumor stroma.

According to some of these embodiments of uses, compositions and/or kits, the neoplasm may be a solid tumor, wherein the anti-cancer agent may be an immunotherapeutic agent, and wherein increased delivery of the immunotherapeutic agent to the tumor is measured by an increase in the presence of infiltrating lymphocytes in the tumor or tumor stroma.

According to some of these embodiments of uses, compositions and/or kits, the neoplasm may be a solid tumor, wherein the anti-cancer agent is radiation, and wherein increased delivery of radiation to the tumor may be measured by a decrease in the size of the tumor as measured by imaging studies.

According to some of these embodiments of uses, compositions and/or kits, the neoplasm may be a solid tumor, wherein the anti-cancer agent may be a gene therapeutic agent, and wherein increased delivery of the gene therapeutic agent to the tumor may be measured by an increase in an immune response in the microenvironment of the tumor.

According to some of these embodiments of uses, compositions and/or kits, wherein the IgE antibody may be an antibody specific to MUC1.

According to some of these embodiments of uses, compositions and/or kits, the antibody specific to MUC1 may bind an epitope of MUC1 selected from SEQ ID NO: 5.

According to some of these embodiments of uses, compositions and/or kits, the heavy chain variable region of the antibody specific to MUC1 may be encoded by a nucleic acid comprising SEQ ID NO: 1 and wherein a light chain variable region of the antibody specific to MUC1 may be encoded by a nucleic acid comprising SEQ ID NO: 2.

According to some of these embodiments of uses, compositions and/or kits, the heavy chain variable region of the antibody specific to MUC1 may be encoded by a nucleic acid comprising SEQ ID NO: 3 and a light chain variable region of the antibody specific to MUC1 may be encoded by a nucleic acid comprising SEQ ID NO: 4.

According to some of these embodiments of uses, compositions and/or kits, the antibody specific to MUC1 may be mAb 3C6.hIgE, mAb 4H5.hIgE or a combination thereof.

According to some of these embodiments of uses, compositions and/or kits, the cancer may be pancreatic cancer, gastric cancer, colorectal cancer, ovarian cancer, breast cancer or lung cancer, and the tumor may be in vivo or in vitro.

According to some of these embodiments of uses, compositions and/or kits, increasing the delivery of the anti-cancer agent may result in a) an increase in the therapeutic index of the anti-cancer agent; b) amelioration of at least one adverse effect of the anticancer agent; c) reduction in the amount of anti-cancer agent used in treatment; d) increase in the permeability of tumor stroma; and e) depletion of the tumor stroma.

According to some of these embodiments of uses, compositions and/or kits, may further comprise contacting the tumor with an anti-cancer agent.

According to some of these embodiments of uses, compositions and/or kits, the anticancer agent may contact with the tumor after the IgE antibody is contacted with the tumor.

According to some of these embodiments of uses, compositions and/or kits, the anti-cancer agent may contact with the tumor before the IgE antibody is contacted with the tumor.

According to some of these embodiments of uses, compositions and/or kits, may further comprise administering an anticancer agent to the subject.

According to some of these embodiments of uses, compositions and/or kits, the anti-cancer agent may be administered to the subject after the IgE antibody is administered to the subject or before the IgE antibody is administered to the subject.

According to some of these embodiments of uses, compositions and/or kits, the anticancer agent may be administered to the subject simultaneously with the IgE antibody.

According to some of these embodiments of uses, compositions and/or kits, the IgE antibody may be specific for an antigen associated with the tumor stroma or a cancer antigen.

IV. Equivalents

Those skilled in the art will recognize, or be able to ascertain using no more than routine experimentation, many equivalents to the specific embodiments of the invention described herein. Such equivalents are intended to be encompassed by the following claims.

V. Examples

The following example is intended to further illustrate certain particularly preferred embodiments of the invention and is not intended to limit the scope of the invention.

Example 1

Evaluation of Vascular Permeability Potential of Anti-MUC1-IgE in Subcutaneous Tumor Model of Pancreatic Cancer In order to first establish the principle of this therapeutic approach, an antibody with suitable specificity and tumor antigen expressing tumor model to be evaluated in an animal tolerant to that tumor antigen are required. A Panc02 tumor cell line transfected with the human MUC1 gene (hMUC1-panc02) is selected. The panc02 tumors are syngeneic to BL6 mice and the hMUC1-panc02 is fully syngeneic to the BL6.Tg mice transgenic for human MUC1. The antibody used for the demonstration experiment is an anti-MUC1-IgE antibody: 3C6.hIgE described above.

Experimental Design

1) Double human transgenic C57BL6/J mice carrying the human transgenes for both human MUC1 and the human FcεRI alpha chain were inoculated subcutaneously with $1 \times 10^6$ hMUC1-panc02 cells subcutaneously. In these mice, the endogenous gene encoding the α-subunit of the high affinity IgE receptor, FcεRIα, has been disrupted, and the mice are transgenic for the human homologue, under the control of the human FcεRIα promoter (Dombrowicz et al., 1996 *J Immunol* 157:1645-1651). In contrast to wild type mice, where FcεRIα expression is limited to mast cells and basophils, the range of expression of FcεRIα in hFcεRI Tg$^+$ mice resembles that seen in humans. In addition to mast cells and basophils, in hFcεRI Tg$^+$ mice (and humans) FcεRI is expressed on eosinophils, monocytes, Langerhans cells, B cells and eosinophils (Kinet, J. P. 1999 *Annu Rev Immunol* 17:931-972; Kayaba et al., 2001 *J Immunol* 167:995-1003). The hFcεRIα gene product has the capacity to complex with the mouse beta and gamma subunits to form a functional 4 chain receptor ($\alpha\beta\gamma_2$). hFcεRI Tg$^+$ mice mount an anaphylactic response to human IgE antibodies and allergen (Dombrowicz et al., 1996 supra). Therefore, in these animals, the full range of myeloid cells participating in stromal modulation that is typical of humans and high primates are recruited, which demonstrates the full principle as conceived for the treatment of human malignancies.

2) anti-MUC1-IgE (25 μg/mouse) along with Dextran, Alexa Fluor® 647 (10,000 Daltons) is injected in the tail vein (100 μl/injection) after the tumor reaches 700-1000 cm$^3$ in size. Control animals are also injected with Dextran, Alexa Fluor® 647 only.

3) Immunofluorescence of Dextran, Alexa Fluor® 647 is observed in the animals at 0 min, 30 min, 2 h, 4 h, 8 h and 24 h post treatment.

Figure 2:
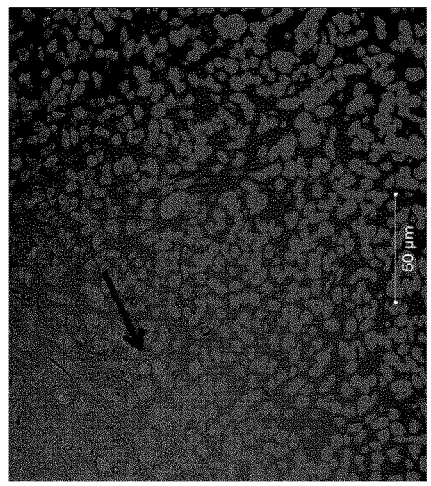
FIG. 2 illustrates the immunofluorescence staining of Dextran, Alexa-Fluor® 647 in Panco2-MUC1 bearing tumor mice.
Figure 2:
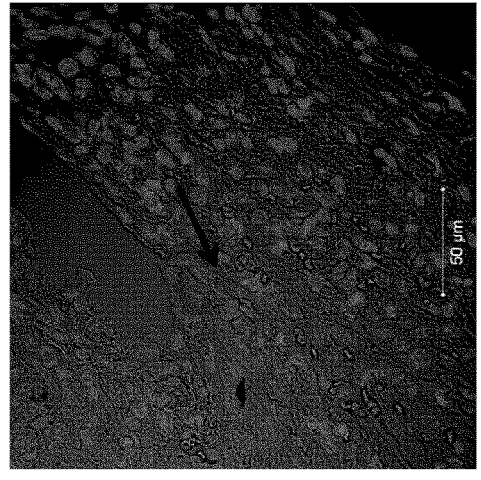
Figure 2:
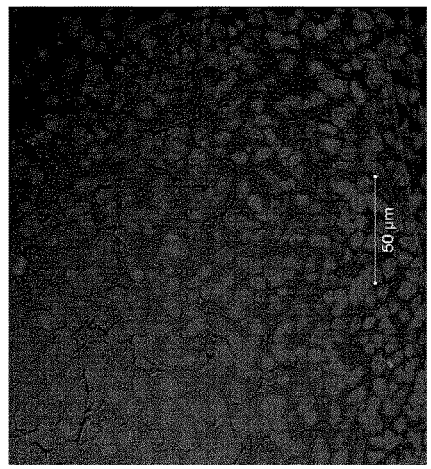
Figure 2:
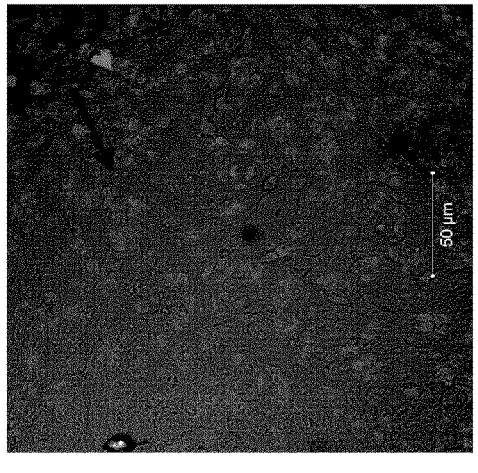
Figure 2:
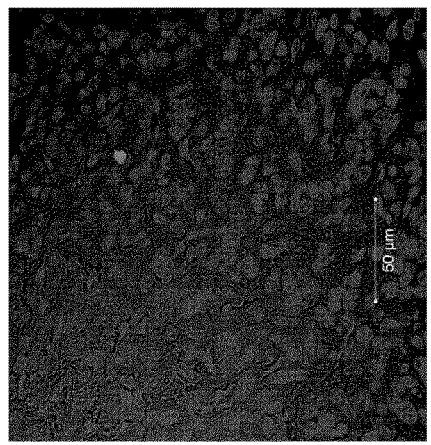
Figure 2:
Figure 3:
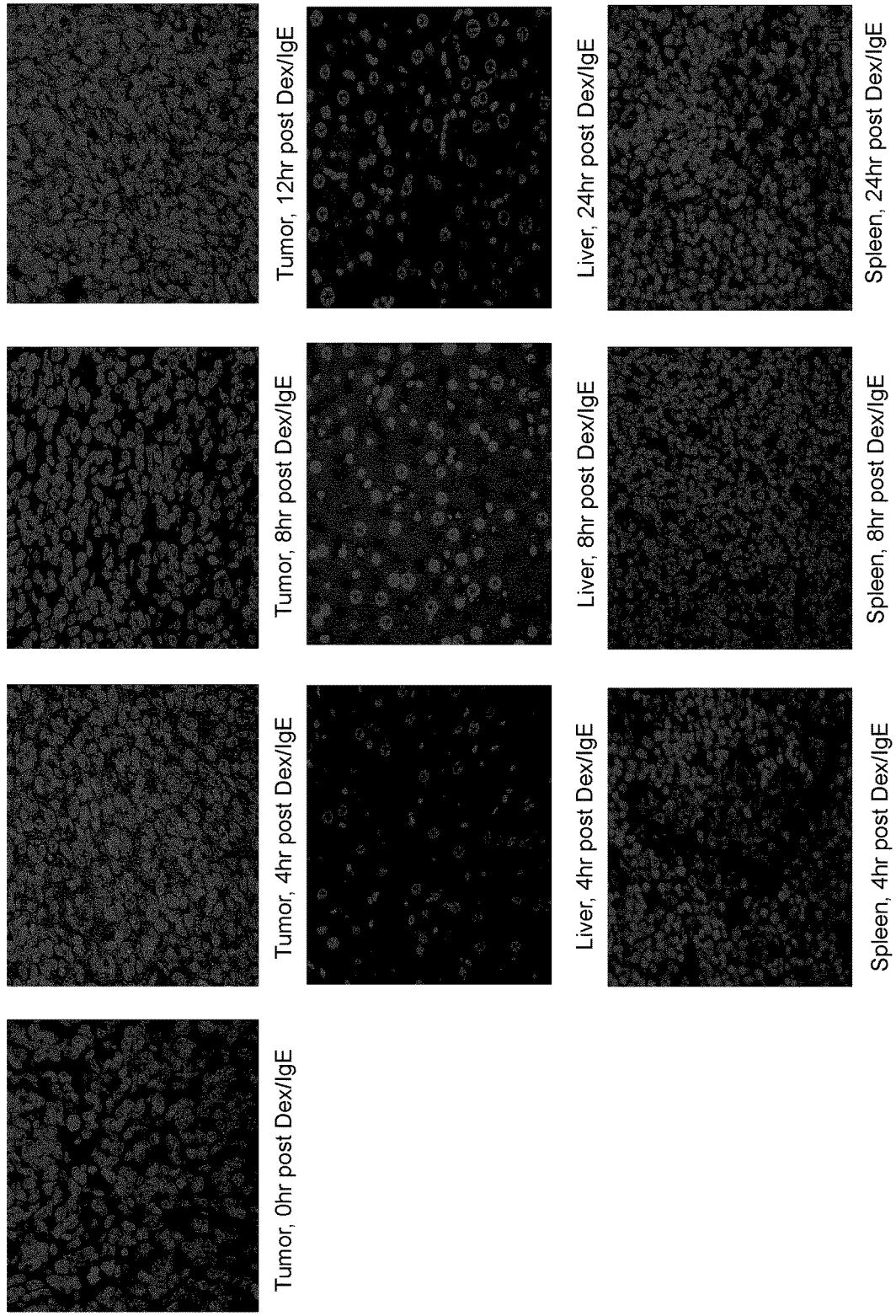
FIG. 3 illustrates the immunofluorescence staining of Dextran, Alexa-Fluor® 647 in Panco2-MUC1 bearing tumor mice
Figure 4:
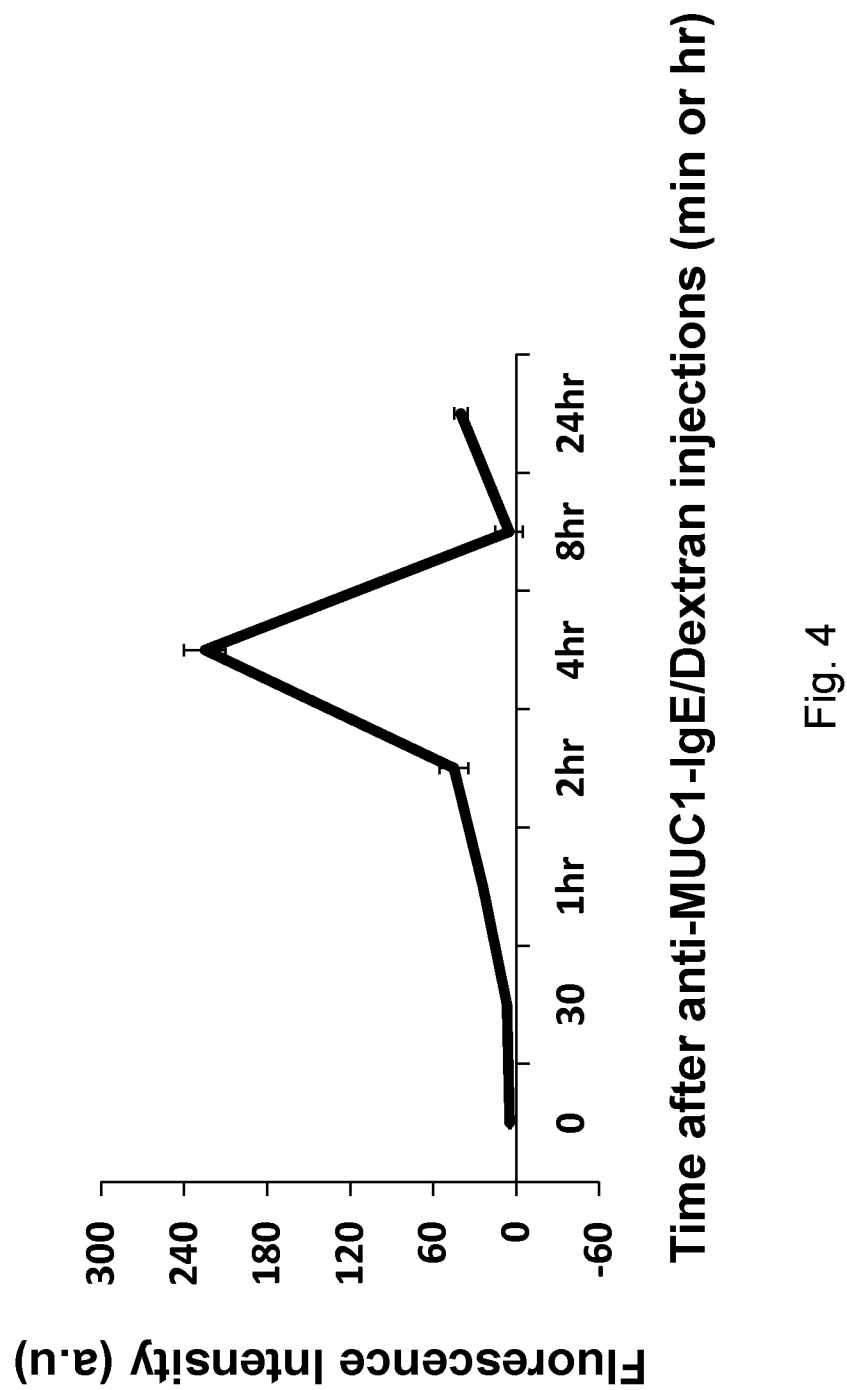
FIG. 4 illustrates a time course for diffusion of Dextran, Alexa-Fluor® 647 in mice tumor post intravenous injection.

See FIG. 1 for an illustration of the experimental design of the present example and FIG. 2 shows light staining appearing after 30 min, and increasing staining after 2 h and 4 h respectively. In absence of anti-MUC1-IgE, no staining is detected. FIG. 3 shows a repeat experiment in which fluorescence intensity is measured at 0, 4, 8, 12 (for tumors) and 24 hours after injection of anti-MUC1-IgE along with Dextran, Alexa Fluor® 647. Again, no staining is observed after immediate injection (0 h), but staining is readily apparent 4 h after injection, and decreased at 8 and 12 h after injection. No staining is observed in the liver and spleen tissues at 4, 8 or 24 h after injection. FIG. 4 illustrates the quantitation of the fluorescence intensity over the course of the experiment, which shows that the fluorescence intensity peaks at about 4 hours post-injection.

Example 2

Mast Cell and Neutrophil Staining in MUC1-Panc02 Tumors

Figure 5:
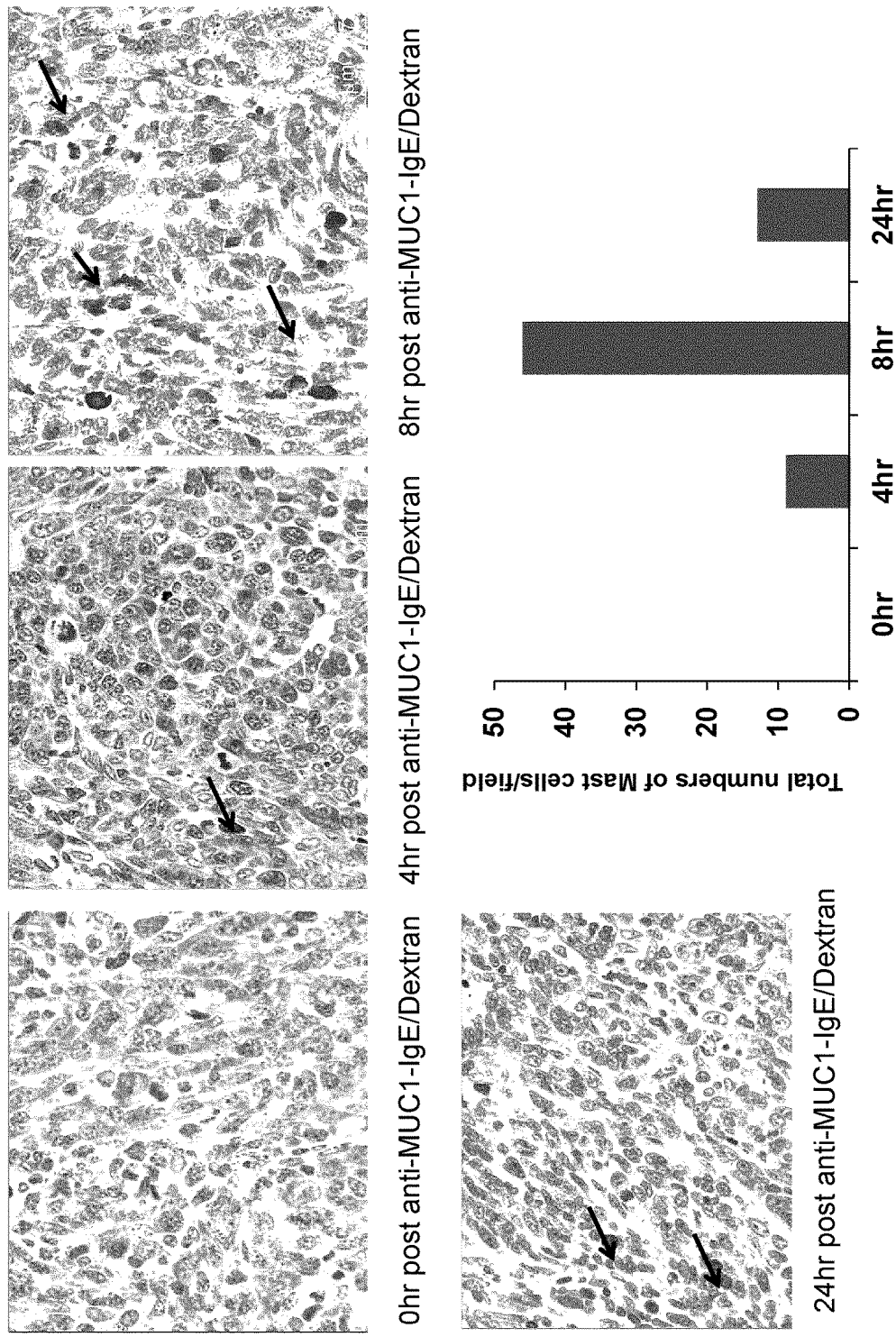
FIG. 5 illustrates the mast cell staining in hMUC1-Panc02 tumor.
Figure 6:
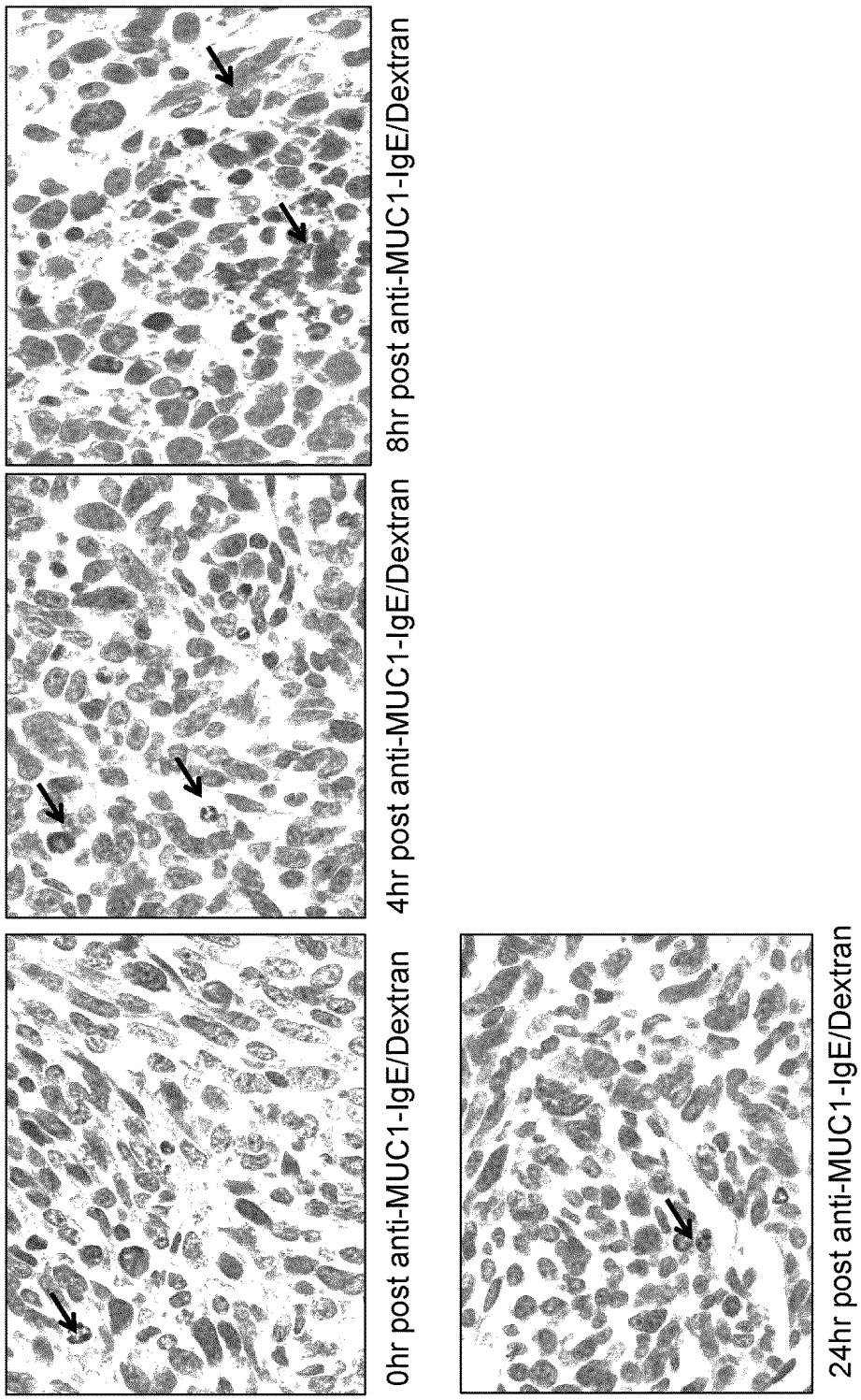
FIG. 6 illustrates the neutrophil staining in the hMUC1-Panc02 tumor.

Next, the infiltration of the tumor with mast cells is evaluated by performing toluidine blue staining in tumor tissue. In contrast, hematoxylin and eosin staining was used for determination of neutrophil (multi-lobed nucleated cells) infiltration in tumor tissue section. FIG. 5 shows that at 0 h, no mast cell can be observed in the tumor tissue, while at 4 h post injection, the appearance of mast cells can be detected, which peaks at 8 h post injection, and remains for at least 24 h post injection. These results show that there in an increased number of mast cells recruited the tumors post injection. On the other hand, FIG. 6 shows that there was no significant change in the number of neutrophils in the tumors post injection.

Example 3

Potentiation of Anti-Tumor Response

Figure 7:
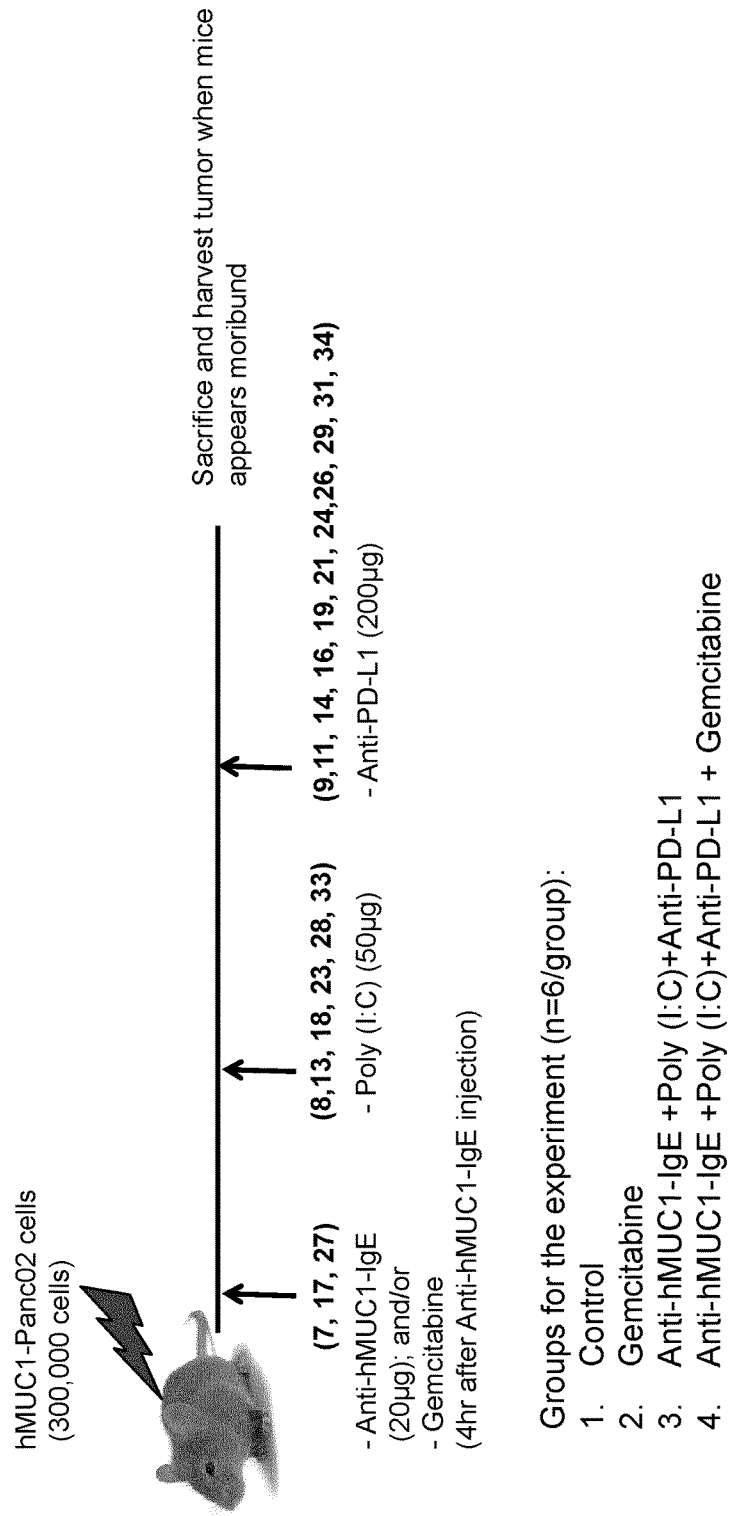
FIG. 7 illustrates an experimental design for testing the method of the present invention.

Again, double human transgenic C57BL6/J mice carrying the human transgenes for both human MUC1 and the human FcεRI alpha chain were inoculated orthotopically with a total of $3\times10^5$ hMUC1-Panc02 cells expressing human MUC1 in these pancreatic tumor cells. Treatments began 7 days after injection of the tumor cells, as per the experimental plan presented in FIG. 7. The experiment included 4 groups of 6 animals, including a control group receiving (0.9% saline), a group receiving gemcitabine alone, a group receiving anti-PDL-1, Poly (1:0) (Hiltonol®) and anti-hMUC1-IgE; and a group receiving anti-PDL-1 and Poly (1:0), anti-hMUC1-IgE and gemcitabine. Specifically, the treatment occurred as follows: anti-hMUC1-IgE (20 μg) and/or Gemcitabine were administered on days 7, 17 and 27. When administered together, the gemcitabine was administered 4 hr after anti-hMUC1-IgE injection. Poly (I:C) (Hiltonol®) (50 μg) was administered on days 8, 13, 18, 23, 28, 33, and anti-PD-L1 (200 μg) was administered on days 9, 11, 14, 16, 19, 21, 24, 26, 29, 31, 34.

Mice bearing orthotopic tumors were followed for growth until animals are sacrificed and tumor harvested when animals became moribund, as per institutional animal care requirements.

Figure 8:
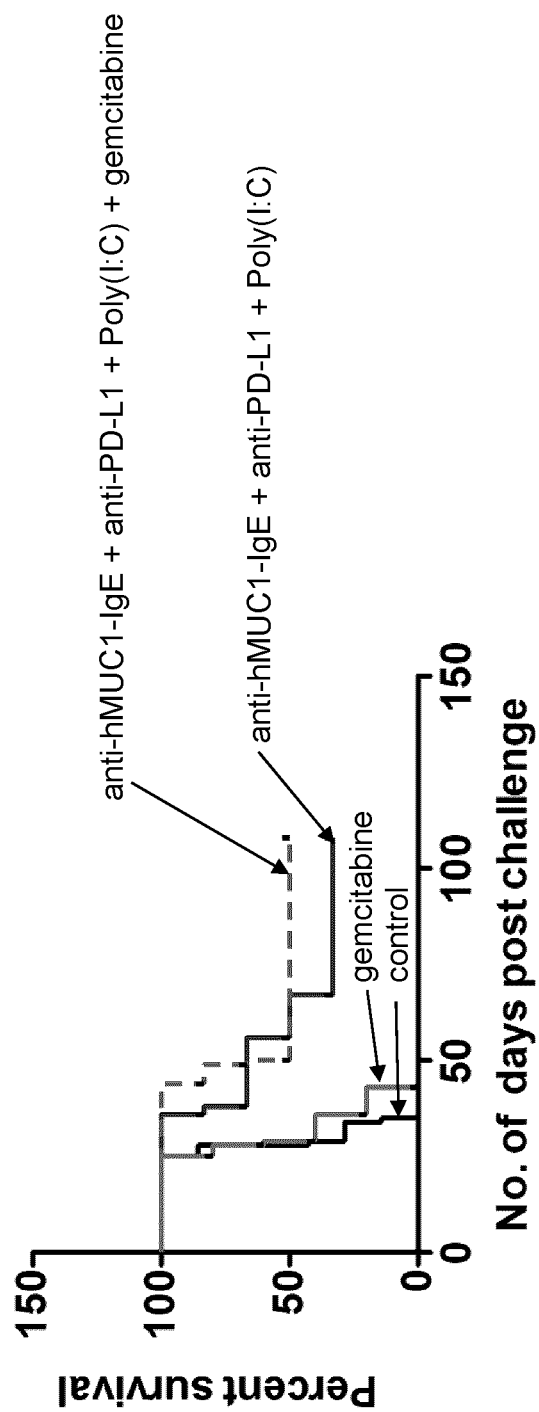
FIG. 8 illustrates that anti-MUC1-IgE can potentiate the anti-tumor response of anti-cancer agents by promoting their efficient delivery in the dense tumor stroma.

The results show in FIG. 8 that the combination treatment with anti-MUC1 IgE, with anti-cancer agents (i.e. anti-PDL-1, Poly (I:C) and gemcitabine) results in an increased survival over the almost 108-day challenge period. None of the animals of the other treatment conditions had a similar survival pattern over the same challenge period, displaying sometimes much steeper survival curves over the same period.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims. It should also be understood that the embodiments described herein are not mutually exclusive and that features from the various embodiments may be combined in whole or in part in accordance with the invention.

SEQUENCE LISTING

<120> 3C6.hIgE heavy chain variable:
<212> DNA

SEQ ID NO: 1

GCCGCCACCATGTACTTGGGACTGAACTGTGTATTCATAGTTTTTCTC

TTAAATGGTGTCCAGAGTGAAGTGAAGCTTGAGGAGTCTGGAGGAGGC

TTGGTGCAACCTGGAGGATCCATGAAACTCTCTTGTGCTGCCTCTGGA

TTCACTTTTAGTGACGCCTGGATGGACTGGGTCCGCCAGTCTCCAGAG

AAGGGGCTTGAGTGGGTTGCTGAAATTAGAAGCAAAGCTAATAATCAT

GCAACATACTATGCTGAGTCTGTGAAAGGGAGGTTCACCATCTCAAGA

GATGTTTCCAAAAGTAGTGTCTACCTGCAAATGAACAACTTAAGAGCT

GAAGACACTGGCATTTATTACTGTACCAGGGGGGGGTACGGCTTTGAC

TACTGGGGCCAAGGCACCACTCTCACAGTCTCCTCAGGTAAGTG

<120> 3C6.hIgE light chain variable:
<212> DNA

SEQ ID NO: 2

GCCGCCACCATGAAGTTGCCTGTTAGGCTGTTGGTGCTGATGTTCTGG

ATTCCTGCTTCCAGCAGTGATGTTTTGATGACCCAAACTCCACTCTCC

CTGCCTGTCAGTCTTGGAGATCAAGCCTCCATCTCTTGCAGATCTAGT

CAGAGCATTGTACATAGTAATGGAAACACCTATTTAGAATGGTACCTG

CAGAAACCAGGCCAGTCTCCAAAGCTCCTGATCTACAAAGTTTCCAAC

CGATTTTCTGGGGTCCCAGACAGGTTCAGTGGCAGTGGATCAGGGACA

GATTTCACACTCAAGATCAGCAGAGTGGAGGCTGAGGATCTGGGAGTT

TATTACTGCTTTCAAGGTTCACATGTTCCGCTCACGTTCGGTGCTGGG

ACCAAGCTGGAGCTGAAACGTAAGT

<120> 4H5.hIgE monoclonal antibody heavy chain variable region
<212> DNA

SEQ ID NO: 3

GCCGCCACCATGGGATGGAGCTGTATCATGCTCTTTTTGGTAGCAACA

GCAACAGGTGTCCACTCCCAGGTCCAACTGCAGCAGTCTGGGGCTGAA

CTGGTGAAGCCTGGGGCTTCAGTGAAGTTGTCCTGCAAGGCTTCTGGC

TACACCTTCACCAGCTACTATATGTACTGGGTGAAGCAGAGGCCTGGA

CAAGGCCTTGAGTGGATTGGAGAGATTAATCCTAGCAATGGTGGTACT

GACTTCAATGAGAAGTTCAAGAGCAAGGCCACACTGACTGTAGACAAA

TCCTCCAGCACAGCATACATGCAACTCAGCAGCCTGACATCTGCGGAC

TCTGCGGTCTATTACTGTACAAGGGGGGGTGATTACCCCTGGTTTGCT

TACTGGGGCCAAGGGACTCTGGTCACTGTCTCTGCAGGTAAGT

SEQUENCE LISTING

<120> 4H5.hIgE monoclonal antibody heavy chain variable region
<212> DNA
SEQ ID NO: 4

GCCGCCACCATGGATTCACAGGCCCAGGTTCTTATGTTACTGCTGCTA

TGGGTATCTGGTACCTGTGGGGACATTGTGATGTCACAGTCTCCATCC

TCCCTAGCTGTGTCAGTTGGAGAGAAGGTTACTATGAGCTGCAAGTCC

AGTCAGAGCCTTTTATATAGTAGCAATCAAAAGAACTACTTGGCCTGG

TACCAGCAGAAACCAGGGCAGTCTCCTAAACTGCTGATTTACTGGGCA

TCCACTAGGGAATCTGGGGTCCCTGATCGCTTCACAGGCAGTGGATCT

GGGACAGATTTCACTCTCACCATCAGCAGTGTGAAGGCTGAAGACCTG

GCAGTTTATTACTGTCAGCAATATTATAGCTATCCTCTCACGTTCGGT

GCTGGGACCAAGCTGGAGCTGAAACGTAAGT

<120> Amino Acid Sequence of MUC1 epitope
<212> Amino Acid
SEQ ID NO: 5

STAPPAHGVTSAPDTRPAPG

---

SEQUENCE LISTING

<160> NUMBER OF SEQ ID NOS: 5

<210> SEQ ID NO 1
<211> LENGTH: 428
<212> TYPE: DNA
<213> ORGANISM: Artificial Sequence
<220> FEATURE:
<223> OTHER INFORMATION: Synthetic polynucleotide
<220> FEATURE:
<223> OTHER INFORMATION: 3C6.hIgE heavy chain variable:

<400> SEQUENCE: 1
gccgccacca tgtacttggg actgaactgt gtattcatag ttttttctctt aaatggtgtc      60 cagagtgaag tgaagcttga ggagtctgga ggaggcttgg tgcaacctgg aggatccatg     120
aaactctctt gtgctgcctc tggattcact tttagtgacg cctggatgga ctgggtccgc     180
cagtctccag agaaggggct tgagtgggtt gctgaaatta agcaaagc taataatcat     240 gcaacatact atgctgagtc tgtgaaaggg aggttcacca tctcaagaga tgtttccaaa     300
agtagtgtct acctgcaaat gaacaactta agagctgaag acactggcat ttattactgt     360
accagggggg gtacggctt tgactactgg ggccaaggca ccactctcac agtctcctca     420
ggtaagtg                                                              428

<210> SEQ ID NO 2
<211> LENGTH: 409
<212> TYPE: DNA
<213> ORGANISM: Artificial Sequence
<220> FEATURE:
<223> OTHER INFORMATION: Synthetic polynucleotide
<220> FEATURE:
<223> OTHER INFORMATION: 3C6.hIgE light chain variable

<400> SEQUENCE: 2
gccgccacca tgaagttgcc tgttaggctg ttggtgctga tgttctggat tcctgcttcc      60
agcagtgatg ttttgatgac ccaaactcca ctctccctgc ctgtcagtct tggagatcaa     120
gcctccatct cttgcagatc tagtcagagc attgtacata gtaatggaaa cacctattta     180
gaatggtacc tgcagaaacc aggccagtct ccaaagctcc tgatctacaa agtttccaac     240
cgattttctg ggtcccaga caggttcagt ggcagtggat cagggacaga tttcacactc     300
aagatcagca gagtggaggc tgaggatctg ggagtttatt actgctttca aggttcacat     360
gttccgctca cgttcggtgc tgggaccaag ctggagctga aacgtaagt                 409

<210> SEQ ID NO 3

```
<211> LENGTH: 427
<212> TYPE: DNA
<213> ORGANISM: Artificial Sequence
<220> FEATURE:
<223> OTHER INFORMATION: Synthetic polynucleotide
<220> FEATURE:
<223> OTHER INFORMATION: 4H5.hIgE monoclonal antibody heavy chain
      variable region

<400> SEQUENCE: 3
gccgccacca tgggatggag ctgtatcatg ctcttttggg tagcaacagc aacaggtgtc    60
cactcccagg tccaactgca gcagtctggg gctgaactgg tgaagcctgg gcttcagtg    120 aagttgtcct gcaaggcttc tggctacacc ttcaccagct actatatgta ctgggtgaag   180
cagaggcctg gacaaggcct tgagtggatt ggagagatta atcctagcaa tggtggtact   240
gacttcaatg agaagttcaa gagcaaggcc acactgactg tagacaaatc ctccagcaca   300
gcatacatgc aactcagcag cctgacatct gcggactctg cggtctatta ctgtacaagg   360
gggggtgatt accctggtt tgcttactgg ggccaaggga ctctggtcac tgtctctgca   420
ggtaagt                                                             427

<210> SEQ ID NO 4
<211> LENGTH: 415
<212> TYPE: DNA
<213> ORGANISM: Artificial Sequence
<220> FEATURE:
<223> OTHER INFORMATION: Synthetic polynucleotide
<220> FEATURE:
<223> OTHER INFORMATION: 4H5.hIgE monoclonal antibody heavy chain
      variable region

<400> SEQUENCE: 4
gccgccacca tggattcaca ggcccaggtt cttatgttac tgctgctatg ggtatctggt    60
acctgtgggg acattgtgat gtcacagtct ccatcctccc tagctgtgtc agttggagag   120
aaggttacta tgagctgcaa gtccagtcag agccttttat atagtagcaa tcaaaagaac   180
tacttggcct ggtaccagca gaaaccaggg cagtctccta aactgctgat ttactgggca   240
tccactaggg aatctggggt ccctgatcgc ttcacaggca gtggatctgg gacagatttc   300
actctcacca tcagcagtgt gaaggctgaa gacctggcag tttattactg tcagcaatat   360
tatagctatc ctctcacgtt cggtgctggg accaagctgg agctgaaacg taagt        415

<210> SEQ ID NO 5
<211> LENGTH: 20
<212> TYPE: PRT
<213> ORGANISM: Homo sapiens
<220> FEATURE:
<223> OTHER INFORMATION: Amino Acid Sequence of MUC1 epitope

<400> SEQUENCE: 5

Ser Thr Ala Pro Pro Ala His Gly Val Thr Ser Ala Pro Asp Thr Arg
1               5                   10                  15

Pro Ala Pro Gly
            20
```

The invention claimed is:

1. A method of treating a solid tumor, comprising administering to a subject in need thereof:
   (a) a therapeutically effective amount of an IgE monoclonal antibody specific to MUC1 having a heavy chain variable region encoded by SEQ ID NO:1 and a light chain variable region encoded by SEQ ID NO:2;
   (b) gemcitabine;
   (c) a poly (I:C);
   (d) an anti-PD-L1 antibody;
   wherein the IgE monoclonal antibody is administered at least 30 minutes to 4 hours prior to administration of the gemcitabine;
   wherein the poly (I:C) is first administered after first administration of the IgE monoclonal antibody and the gemcitabine;
   wherein the poly (I:C) is administered 6 hours to 48 hours after administration of the gemcitabine; and
   wherein the anti-PD-L1 antibody is first administered 6 hours to 48 hours after first administration of the poly (I:C).

2. The method of claim 1, wherein the IgE monoclonal antibody is specific to MUC1 associated with the solid tumor's microenvironment.

3. The method of claim 1, wherein the solid tumor's is pancreatic cancer, gastric cancer, colorectal cancer, ovarian cancer, breast cancer, or lung cancer.

4. The method of claim 1,
   wherein the poly (I:C) is administered to the subject every second day.

5. The method of claim 4,
   wherein the anti-PD-L1 antibody is administered to the subject alternatingly every second and third day.

6. The method of claim 1, further comprising performing the method one additional time.

7. The method of claim 1, further comprising performing the method two additional times.

8. The method of claim 1, wherein the poly (I:C) is administered to the subject every fifth day; and the anti-PD-L1 antibody is administered to the subject alternatingly every second and third day.

* * * * *